United States Patent
Chute et al.

(10) Patent No.: US 10,822,299 B2
(45) Date of Patent: Nov. 3, 2020

(54) COMPOUNDS AND METHODS FOR HEMATOPOIETIC REGENERATION

(71) Applicant: The Regents of the University of California, Oakland, CA (US)

(72) Inventors: John P. Chute, Sherman Oaks, CA (US); Michael E. Jung, Los Angeles, CA (US); Emelyne Diers, Scotland (GB)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/304,427

(22) PCT Filed: May 26, 2017

(86) PCT No.: PCT/US2017/034772
§ 371 (c)(1),
(2) Date: Nov. 26, 2018

(87) PCT Pub. No.: WO2017/205795
PCT Pub. Date: Nov. 30, 2017

(65) Prior Publication Data
US 2019/0292132 A1  Sep. 26, 2019

Related U.S. Application Data

(60) Provisional application No. 62/341,722, filed on May 26, 2016.

(51) Int. Cl.
| | |
|---|---|
| C07C 225/16 | (2006.01) |
| A61P 7/06 | (2006.01) |
| C07C 225/22 | (2006.01) |
| C07C 233/31 | (2006.01) |
| C07C 311/39 | (2006.01) |
| C07D 211/58 | (2006.01) |
| C07D 231/12 | (2006.01) |
| C07D 307/52 | (2006.01) |
| C07D 317/66 | (2006.01) |
| C07D 333/22 | (2006.01) |
| C07F 7/18 | (2006.01) |
| C07C 311/44 | (2006.01) |
| C07C 205/37 | (2006.01) |
| C07D 295/205 | (2006.01) |
| C07D 307/46 | (2006.01) |

(52) U.S. Cl.
CPC .............. *C07C 225/16* (2013.01); *A61P 7/06* (2018.01); *C07C 205/37* (2013.01); *C07C 225/22* (2013.01); *C07C 233/31* (2013.01); *C07C 311/39* (2013.01); *C07C 311/44* (2013.01); *C07D 211/58* (2013.01); *C07D 231/12* (2013.01); *C07D 295/205* (2013.01); *C07D 307/46* (2013.01); *C07D 307/52* (2013.01); *C07D 317/66* (2013.01); *C07D 333/22* (2013.01); *C07F 7/1804* (2013.01); *C07C 2601/02* (2017.05); *C07C 2601/14* (2017.05)

(58) Field of Classification Search
CPC .................................. C07C 225/16; A61P 7/06
See application file for complete search history.

(56) References Cited

U.S. PATENT DOCUMENTS

| | | | |
|---|---|---|---|
| 9,980,943 B2* | 5/2018 | Burkin | ................. A61K 31/404 |
| 10,398,749 B2* | 9/2019 | Burkin | ................... A61K 31/41 |

FOREIGN PATENT DOCUMENTS

| | | |
|---|---|---|
| CN | 104119285 A | 10/2014 |
| CN | 106279027 A | 1/2017 |
| CN | 106631865 A | 5/2017 |
| CN | 107325018 A | 11/2017 |
| EP | 0779291 A1 | 6/1997 |
| EP | 0779292 A1 | 6/1997 |
| JP | 563239273 A | 10/1988 |
| WO | WO-2008/021389 A2 | 2/2008 |
| WO | WO-2012/135416 A1 | 10/2012 |
| WO | WO-2013/082751 A1 | 6/2013 |
| WO | WO-2013/096971 A1 | 6/2013 |
| WO | WO-2014/033122 A1 | 3/2014 |
| WO | WO-2016/081808 A1 | 5/2016 |
| WO | WO-2017/205795 A1 | 11/2017 |
| WO | WO-2019/108800 A1 | 6/2019 |

OTHER PUBLICATIONS

International Search Report and Written Opinion for International Application No. PCT/US2017/034772 dated Aug. 16, 2017.
Jeragh et al., "Enaminone Complexes: Synthesis, Characterization and Bioactivity," Chem Sci Trans, 4: 113-120 (2015).
Martin et al., "Identification of small molecule inhibitors of PTPs through an integrative virtual and biochemical approach," PLoS One, 7(11):e50217 (2012).
Pintori et al., "Insertion of benzene rings into the amide bond: one-step synthesis of acridines and acridones from aryl amides," Org Lett, 12(1): 168-171 (2010).
Quarmyne et al., "Protein tyrosine phosphatase-σ regulates hematopoietic stem cell-repopulating capacity," J Clin Invest, 125(1): 177-182 (2015).
CAS Registry No. 369392-83-6 (2001).
CAS Registry No. 380877-28-1 (2002).
CAS Registry No. 416884-32-7 (2002).
Database Registry Chemical Abstracts, Database Accession No. 1478709-91-9, CAS Registry No. 1478709-91-9 (Nov. 23, 2013).
Database Registry Chemical Abstracts, Database Accession No. 332353-84-1, CAS Registry No. 332353-84-1 (Apr. 25, 2001).
Database Registry Chemical Abstracts, Database Accession No. 404837-39-4, CAS Registry No. 404837-39-4 (Apr. 9, 2002).

(Continued)

*Primary Examiner* — Golam M Shameem
(74) *Attorney, Agent, or Firm* — Foley Hoag LLP; David P. Halstead; Lucas P. Watkins

(57) ABSTRACT

The invention relates to compounds that promote hematopoietic regeneration. The invention further relates to methods of promoting hematopoietic regeneration using the novel compounds of the invention.

16 Claims, 10 Drawing Sheets

(56) References Cited

OTHER PUBLICATIONS

Database Registry Chemical Abstracts, Database Accession No. 424810-44-6, CAS Registry No. 424810-44-6 (Jun. 3, 2002).
Database Registry Chemical Abstracts, Database Accession No. 431917-07-6, CAS Registry No. 431917-07-6 (Jun. 18, 2002).
Database Registry Chemical Abstracts, Database Accession No. 444568-74-5, CAS Registry No. 444568-74-5 (Aug. 21, 2002).
Database Registry Chemical Abstracts, Database Accession No. 94298-88-1, CAS Registry No. 94298-88-1 (Jan. 21, 1985).
International Search Report and Written Opinion for International Application No. PCT/US2018/063074 dated Mar. 3, 2019.
Wang et al., "ZnCl2-catalyzed chemoselective cascade reactions of enaminones with 2-furylcarbinols: a versatile process for the synthesis of cyclopenta [b] pyrrole derivatives," Chemical Communications, 50(17):2164-2166 (2014).
Zarzycka et al., "Discovery of small molecule CD40-TRAF6 inhibitors," J Chem Inf Model, 55(2): 294-307 (2015).
Borah et al., "DMF Dimethyl Acetal as Carbon Source for α-Methylation of Ketones: A Hydrogenation-Hydrogenolysis Strategy of Enaminones," J Org Chem, 80(9): 4722-4728 (2015).
Chen et al., "One-pot oxidation and rearrangement of propargylamines and in situ pyrazole synthesis," Org Lett, 16 (16): 4146-4149 (2014).
De Kimpe et al., "Reactivity of n-aryl-α, α-dichlorinated arylketimines," Tetrahedron, 35(6): 789-798 (1979).
Dissanayake et al., "Single-step synthesis of pyrazoles using titanium catalysis; incl. Supplementary information," Chem Comm 48(3):440-442 (2012).
Gompper et al., "Reactions of α,(β-unsaturated β-amino- and β-hydroxycarbonyl compounds with sulfur monochloride and related compounds," Justus Liebigs Annalen der Chemie 675:151-174 (1964).
King et al., "The triflic acid-mediated cyclisation of N-benzylcinnamanilides," Tetrahedron, 69(40):8592-8601 (2013).

Park et al., "Discovery of novel protein tyrosine phosphatase sigma inhibitors through the virtual screening with modified scoring function," Med Chem Res, 23(2): 1016-1022 (2014).
Park et al., "Discovery of potent inhibitors of receptor protein tyrosine phosphatase sigma through the structure-based virtual screening," Bioorg Med Chem Lett, 22(20): 6333-6337 (2012).
Pina et al., "Synthesis and prototropic isomerization of 1-nitrophenyl1-2-acylpyrroles," Chemistry of Heterocyclic Compounds, 25(3):268-271 (1989).
Radinov et al., "Benzo[b][1,6]naphthyridines and pyrimido[4,5-b]quinolines from 3-benzoyl-4-chloropyridine and 5-benzoyl-4,6-benzoyl1-4,6-dichloropyrimidine," Izvestiya po Khimiya, 22(1):144-157 (1989).
Shao et al., "Copper-catalyzed selective synthesis of highly substituted pyridones by the reaction of enaminones with alkynes," Synthesis, 44(21): 3301-3306 (2012).
Shao et al., "Lewis acid-catalyzed cyclization of enaminones with propargylic alcohols: regioselective synthesis of multisubstituted 1,2-dihydropyridines," The Journal of Organic Chemistry, 78(11):5731-5736 (2013).
Supplementary European Search Report for EP application No. EP17803701 dated Dec. 2, 2019.
Yang et al., "Acid-Catalyzed Cascade Reactions of Enaminones with Aldehydes: C-H Functionalization to Afford 1,4-Dihydropyridines," Eur J Org Chem, 22: 4189-4193 (2010).
Zhang et al., A small molecule inhibitor of protein tyrosine Phosphatase-Sigma (PTPsigma) promotes Hematopoietic Stem Cell (HSC) regeneration, Blood, 128:822 (2016).
Zhao et al., "Base-Promoted Approach to Highly Functionalized Conjugated Dienes through Enamine Migration: Synthesis of Highly Functionalized Conjugated Dienes," Euro J Org Chem 36:7984-7991 (2015).
Zhao et al., "Gold-catalyzed chemo- and diastereoselective C(sp2)-H functionalization of enaminones for the synthesis of pyrrolo[3,4-c]-quinolin-1-one-derivatives," Org Biomol Chem 14(7):2177-2181 (2016).
International Preliminary Report on Patentability for International Application No. PCT/US2018/063074 dated Jun. 2, 2020.
U.S. Appl. No. 16/767,919, Pending.

* cited by examiner

COMPOUNDS AND METHODS FOR HEMATOPOIETIC REGENERATION

REFERENCE TO RELATED APPLICATIONS

This application is a national-stage filing under 35 U.S.C. 371 of International Application PCT/US2017/034772, filed May 26, 2017, which claims the benefit of U.S. Provisional Application No. 62/341,722, filed May 26, 2016; the contents of each of which are fully incorporated by reference herein.

STATEMENT REGARDING FEDERALLY SPONSORED RESEARCH OR DEVELOPMENT

This invention was made with Government support under grant number AI067769, awarded by the National Institutes of Health. The Government has certain rights in the invention.

BACKGROUND OF THE INVENTION

Hematopoietic stem cells (HSCs) possess the unique capability to undergo self-renewal and give rise to all of the mature components of the hematologic and immune systems throughout the lifetime of an individual. HSC self-renewal is regulated by intrinsic mechanisms as well as extrinsic signaling emanating from the bone marrow (BM) microenvironment or niche. However, the precise mechanisms through which BM microenvironment cells regulate HSC self-renewal are incompletely understood. Furthermore, the mechanisms governing HSC regeneration, which is necessary for hematologic recovery to occur in patients receiving myelosuppressive chemotherapy, radiotherapy and hematopoietic cell transplantation, remain poorly understood.

The transmembrane tyrosine phosphatase PTPσ (also known as PTPRS) has been discovered to regulate murine and human HSC self-renewal and regeneration in vivo. The loss of PTPσ substantially increases long-term HSC-repopulating capacity.

Currently, there are no FDA-approved systemic growth factors that promote human HSC regeneration or multilineage hematologic recovery in patients. Granulocyte colony stimulating factor (GCSF, Neupogen) is a white blood cell (WBC)-specific growth factor that accelerates neutrophil recovery in patients receiving chemotherapy and likely is detrimental to HSC function. Erythropoietin (Epogen) is a red blood cell (RBC)-specific growth factor which promotes RBC production in anemic patients due to chronic illness. Since PTPσ inhibitors target HSCs which give rise to entirety of the hematopoietic and immune systems, our proposed product would complement or possibly supercede indications for GCSF or erythropoietin. We are not aware of any novel small molecule inhibitors which are specific to PTPσ.

Thus, there is a need for new systemic therapies that can promote the self-renewal or regeneration of hematopoietic stem cells in vivo, and specifically for inhibitors of PTPσ that can have that effect.

SUMMARY OF THE INVENTION

In one aspect, the present invention provides compounds having the structure of formula (I):

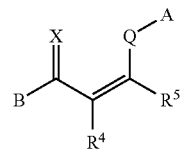

and pharmaceutically acceptable salts and/or prodrugs thereof, wherein the variables are as defined herein. The compounds are typically selective inhibitors of PTPσ. In some embodiments, the compounds promote hematopoietic reconstitution in a subject in need thereof. Compounds of formula (I) can be used to treat conditions described herein.

The present disclosure also provides compositions (such as pharmaceutical compositions) that comprise the compounds of this disclosure. The disclosure also includes the use of the compounds or compositions disclosed herein in the manufacture of a medicament for the treatment of one or more of the conditions described herein.

Another aspect of the disclosure provides methods for treating the conditions described herein using the compounds or compositions disclosed herein, including methods for promoting hematopoietic reconstitution in a subject in need thereof.

DETAILED DESCRIPTION OF THE DRAWINGS

DETAILED DESCRIPTION OF THE INVENTION

Figure 1:
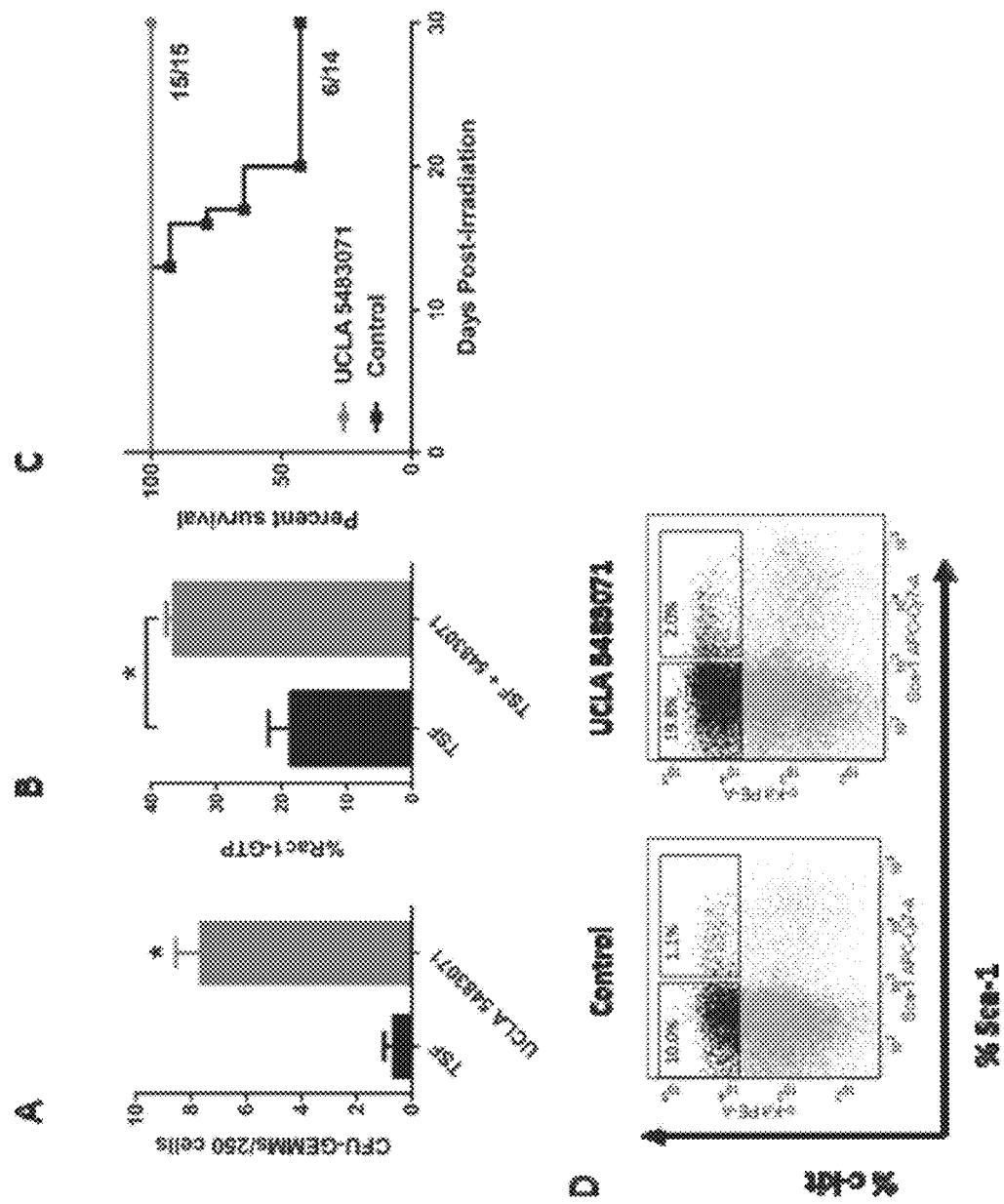
FIG. 1 shows that PTPσ inhibition improves hematologic recovery and survival of irradiated mice.

In one aspect, the present invention provides compounds having the structure of formula (0:

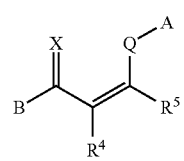

and pharmaceutically acceptable salts and/or prodrugs thereof, wherein:

A is selected from alkyl, alkoxy, cycloalkyl, cycloalkenyl, heterocyclyl, aryl, aralkyl, heteroaryl, and heteroaralkyl, preferably phenyl, furyl, cyclohexyl, or cyclopropyl;

B is aryl or heteroaryl, preferably phenyl;

$R^4$ and $R^5$ are each independently selected from H, alkyl, alkenyl, alkynyl, hydroxy, alkoxy, cycloalkyl, heterocyclyl, aryl, heteroaryl, sulfonyl, and halo, or $R^4$ and $R^5$ together with the ethylene moiety that separates them may form a ring, such as a cycloalkenyl, heterocyclyl, aryl, or heteroaryl;

X is selected from O, S, or $NR^a$, preferably O or $NR^a$;

Q is selected from $NR^a$, O, or S, preferably O or $NR^a$; and each instance of $R^a$ is selected from H, alkyl, alkenyl, alkynyl, hydroxy, alkoxy, silyloxy, cycloalkyl, cycloalkenyl, heterocyclyl, aryl, heteroaryl, amino, sulfonyl, carbonyl, nitro, halo and cyano, or, when X and Q are both $NR^a$, two occurrences of $R^a$ together represent a single bond between X and Q.

In certain embodiments, A is selected from alkyl, cycloalkyl, cycloalkenyl, or heterocyclyl. In further embodiments, A is selected from methyl, ethyl, propyl, cyclopropyl, n-butyl, sec-butyl, tert-butyl, cyclobutyl, cyclopentyl, cyclohexyl, piperidinyl, or piperazinyl.

In certain embodiments, A is selected from aryl, aralkyl, heteroaryl, or heteroaralkyl. In further embodiments, A is selected from phenyl, benzyl, furanylmethyl, naphthyl, or benzodioxole.

In certain embodiments, A is substituted with $R^1$ and $R^2$, and is optionally further substituted, wherein $R^1$ and $R^2$ are each independently selected from H, alkyl, alkenyl, alkynyl, hydroxy, alkoxy, silyloxy, cycloalkyl, heterocyclyl, aryl, heteroaryl, amino, sulfonyl, carbonyl, nitro, halo and cyano. $R^1$ and $R^2$ may be independently selected from alkyl, alkenyl, alkynyl, hydroxy, alkoxy, silyloxy, cycloalkyl, heterocyclyl, aryl, heteroaryl, amino, sulfonyl, carbonyl, nitro, halo and cyano. In certain embodiments, $R^1$ and $R^2$ are independently selected from H, alkyl, alkenyl, alkynyl, hydroxy, alkoxy, silyloxy, cycloalkyl, heterocyclyl, aryl, heteroaryl, sulfonyl, carbonyl, nitro, halo and cyano. In certain embodiments, $R^1$ and $R^2$ are independently selected from alkyl, alkenyl, alkynyl, hydroxy, alkoxy, silyloxy, cycloalkyl, heterocyclyl, aryl, heteroaryl, sulfonyl, carbonyl, nitro, halo and cyano.

In certain embodiments, B is selected from phenyl, furanyl, cyclohexyl, thiophene, or naphthyl. In certain embodiments, B is phenyl. In some embodiments, B is optionally substituted with up to n instances of $R^3$, wherein n is 0, 1, 2, 3, 4, or 5, and each instance of $R^3$ is independently selected from alkyl, alkenyl, alkynyl, hydroxy, alkoxy, silyloxy, cycloalkyl, cycloalkenyl, heterocyclyl, aryl, heteroaryl, amino, sulfonyl, carbonyl, nitro, halo and cyano;

In certain embodiments, $R^4$ and $R^5$ are each independently selected from H, alkyl, or cycloalkyl; or $R^4$ and $R^5$ together with the ethylene moiety that separates them form a phenylene ring. In certain embodiments, $R^4$ and $R^5$ are each H.

In certain embodiments, X is O and Q is $NR^a$.

In certain embodiments, compounds of formula (I) have the structure of formula (II):

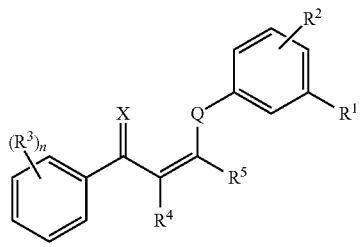

(II)

and pharmaceutically acceptable salts and/or prodrugs thereof, wherein n, X, Q, $R^1$, $R^2$, $R^3$, $R^4$, and $R^5$ are as defined herein.

In certain embodiments, compounds of formula (I) or (II) are enriched in stereoisomers in which the —(C=X)— and -Q-moieties are disposed in a cis configuration or a trans configuration.

In certain embodiments, compounds of formula (II) or (III) have the structure of formula (IIIa):

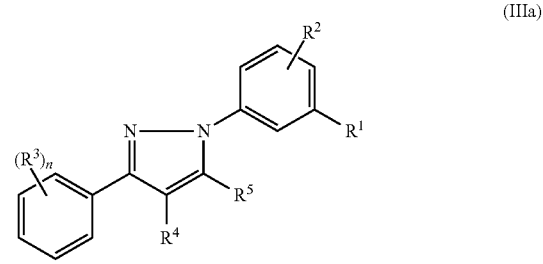

(IIIa)

and pharmaceutically acceptable salts and/or prodrugs thereof, wherein $R^1$, $R^2$, $R^3$, n, $R^4$, and $R^5$ are as defined herein.

In certain embodiments, compounds of formula (II) have the structure of formula (IIa):

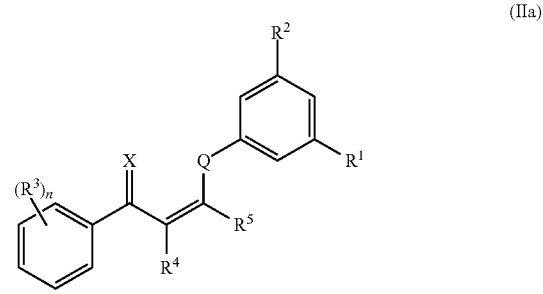

(IIa)

and pharmaceutically acceptable salts and/or prodrugs thereof, wherein n, X, Q, $R^1$, $R^2$, $R^3$, $R^4$, and $R^5$ are as defined herein.

In certain preferred embodiments, n is 0 or 1, most preferably 0.

In certain preferred embodiments, X is O.

In certain preferred embodiments, Q is NH.

In certain embodiments, compounds of formula (IIa) have the structure of formula (IIb):

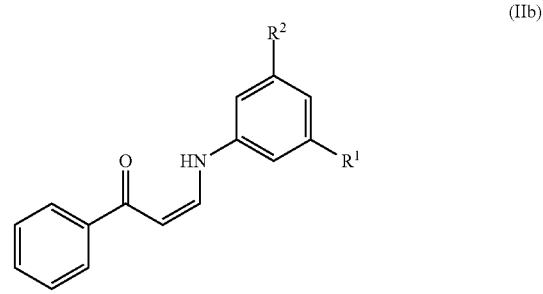

(IIb)

or a pharmaceutically acceptable salt and/or prodrug thereof, wherein $R^1$ and $R^2$ are as defined herein.

In certain embodiments, compounds of formula (IIa) have the structure of formula (IIc):

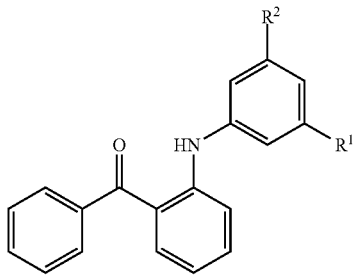

(IIc)

and pharmaceutically acceptable salts and/or prodrugs thereof, wherein $R^1$ and $R^2$ are as defined herein.

In certain embodiments, $R^1$ and $R^2$ are each independently selected from H, alkyl, alkenyl, alkynyl, hydroxy, alkoxy, cycloalkyl, heterocyclyl, aryl, heteroaryl, amino, sulfonyl, carbonyl, nitro, halo and cyano.

In certain embodiments, $R^1$ is selected from H, alkyl, alkenyl, alkynyl, hydroxy, alkoxy, cycloalkyl, heterocyclyl, aryl, heteroaryl, amino, sulfonyl, carbonyl, nitro, halo and cyano; and $R^2$ is selected from alkyl, alkenyl, alkynyl, alkoxy, cycloalkyl, heterocyclyl, aryl, heteroaryl, amino, sulfonyl, carbonyl, halo and cyano.

In certain embodiments, $R^1$ and $R^2$ are each independently selected from alkyl, alkenyl, alkynyl, hydroxy, alkoxy, cycloalkyl, heterocyclyl, aryl, heteroaryl, amino, sulfonyl, carbonyl, nitro, halo and cyano.

In certain embodiments, $R^1$ and $R^2$ are independently selected from $C_1$-$C_4$ alkyl, hydroxy, $C_1$-$C_4$ alkoxy, $C_1$-$C_8$ alkylsilyloxy, $C_1$-$C_4$ alkoxycarbonyl, nitro, and halo. In certain embodiments, $R^1$ and $R^2$ are independently selected from $C_1$-$C_3$ alkyl, hydroxy, $C_1$-$C_3$ alkoxy, nitro, and halo.

In certain preferred embodiments, $R^1$ and $R^2$ are independently selected from H, methyl, trifluoromethyl, fluoro, methoxy, hydroxy, N,N-dimethylsulfonyl, tert-butoxycarbonyl, or tert-butyldimethylsilyloxy (TBDMS-oxy). In certain preferred embodiments, $R^1$ and $R^2$ are independently selected from H, methyl, trifluoromethyl, fluoro, methoxy, hydroxy, or N,N-dimethylsulfonyl.

In certain preferred embodiments, $R^1$ and $R^2$ are both fluoro.

In certain embodiments, if n is 0 and $R^1$ is H, then $R^2$ is not H, nitro, hydroxy, methoxy, or silyloxy.

In certain embodiments, a compound of Formula (IIc) is compound DJ027.

In certain embodiments, compounds of Formula (I) are selected from the compounds of Table 1:

TABLE 1

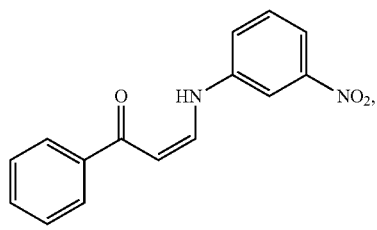

DJ001

M.wt: 268.2720

TABLE 1-continued

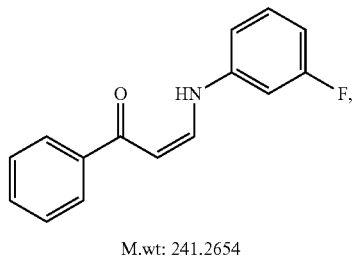 [SMILES: O=C(/C=C\Nc1cccc(F)c1)c1ccccc1]

DJ002

M.wt: 241.2654

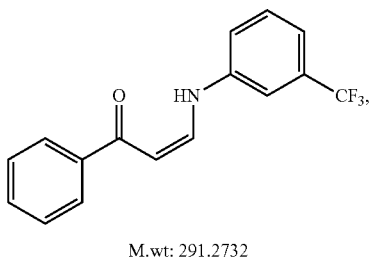 [SMILES: O=C(/C=C\Nc1cccc(C(F)(F)F)c1)c1ccccc1]

DJ003

M.wt: 291.2732

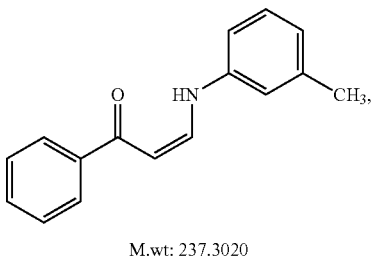 [SMILES: Cc1cccc(N/C=C\C(=O)c2ccccc2)c1]

DJ004

M.wt: 237.3020

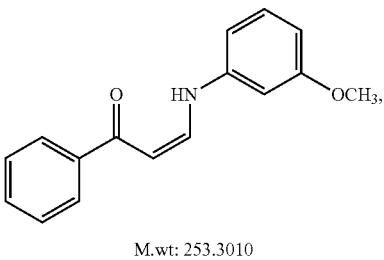 [SMILES: COc1cccc(N/C=C\C(=O)c2ccccc2)c1]

DJ005

M.wt: 253.3010

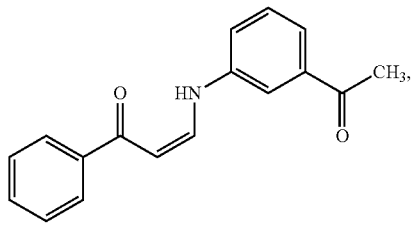

DJ006

M.wt: 265.3120

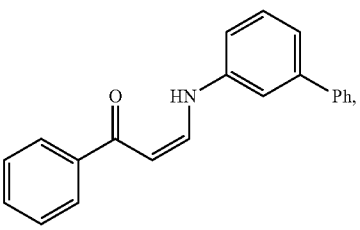

DJ007

M.wt: 299.3730

TABLE 1-continued
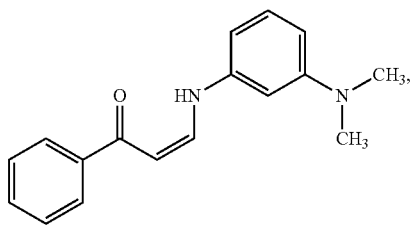
M.wt: 266.3440 DJ008
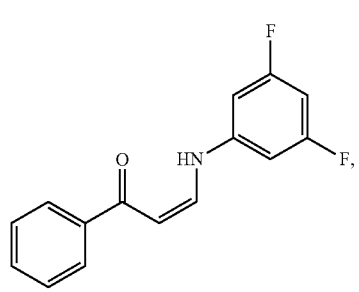
M.wt: 259.2558 DJ009
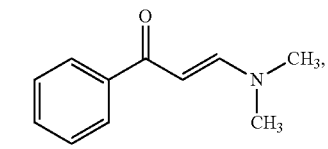
M.wt: 175.2310 DJ010
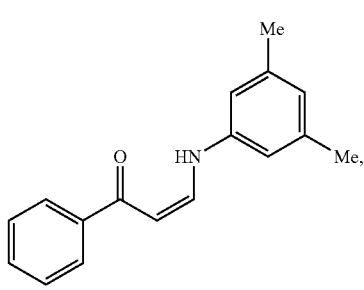
M.wt: 251.3290 DJ011
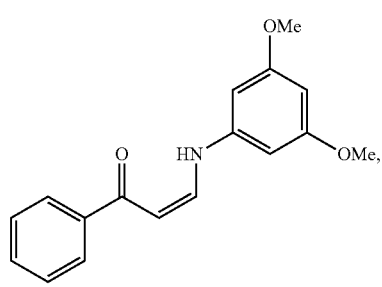
M.wt: 283.3270 DJ012
TABLE 1-continued
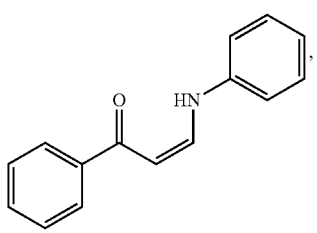
M.wt: 223.2750 DJ013
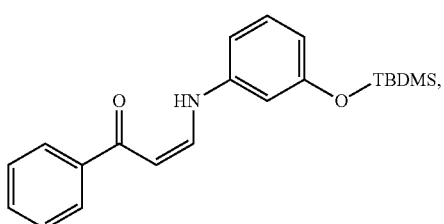
M.wt: 353.5370 DJ014
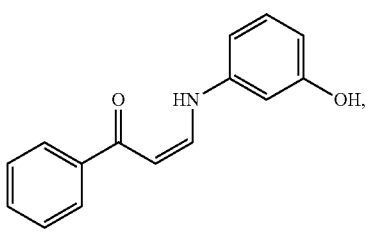
M.wt: 239.2740 DJ015
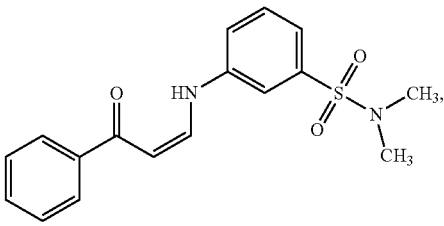
M.wt: 330.4020 DJ016
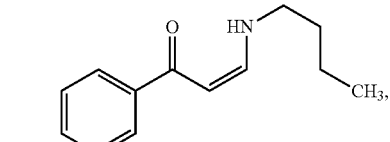
M.wt: 203.2850 DJ017
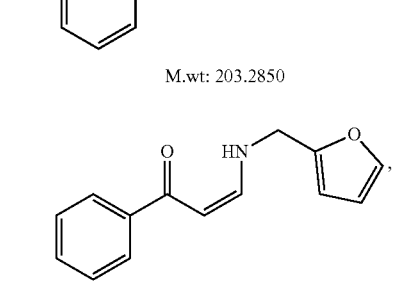
M.wt: 227.2360 DJ018

TABLE 1-continued
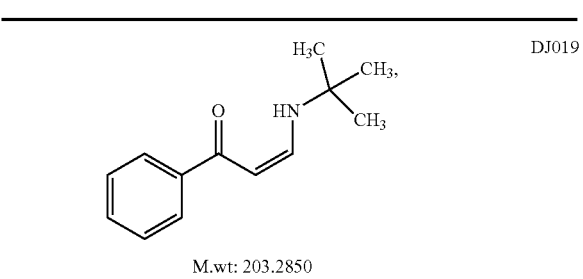
M.wt: 203.2850 — DJ019
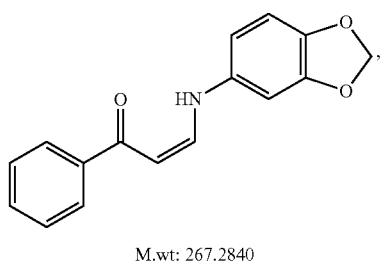 [SMILES: O=C(/C=C\Nc1ccc2c(c1)OCO2)c1ccccc1]
M.wt: 267.2840 — DJ020
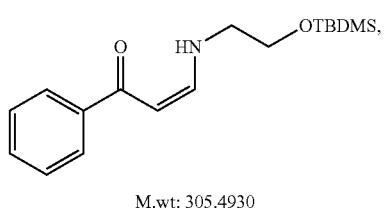 [SMILES: CC(C)(C)[Si](C)(C)OCCN/C=C\C(=O)c1ccccc1]
M.wt: 305.4930 — DJ021
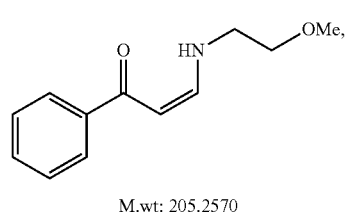 [SMILES: COCCN/C=C\C(=O)c1ccccc1]
M.wt: 205.2570 — DJ022
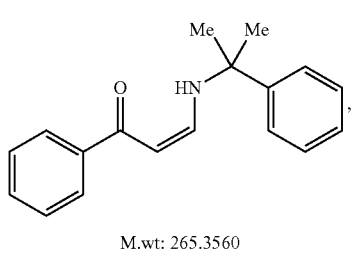 [SMILES: CC(C)(N/C=C\C(=O)c1ccccc1)c1ccccc1]
M.wt: 265.3560 — DJ023
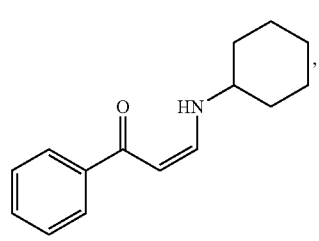
M.wt: 229.3230 — DJ024
TABLE 1-continued
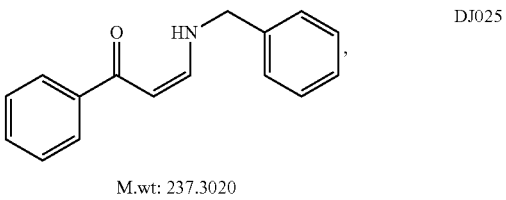
M.wt: 237.3020 — DJ025
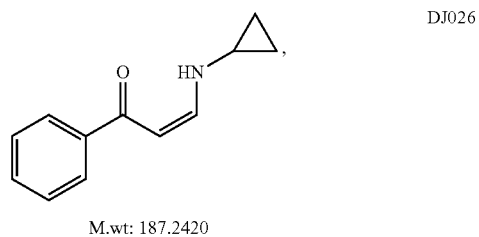
M.wt: 187.2420 — DJ026
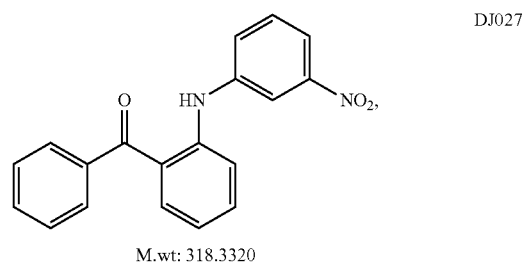
M.wt: 318.3320 — DJ027
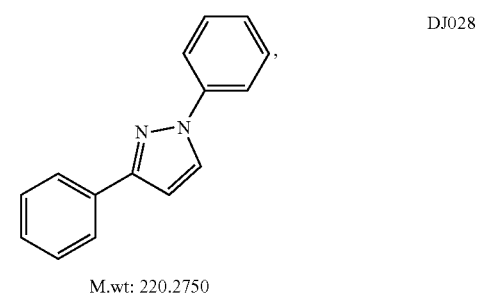
M.wt: 220.2750 — DJ028
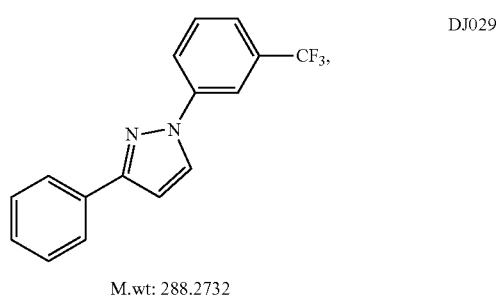
M.wt: 288.2732 — DJ029
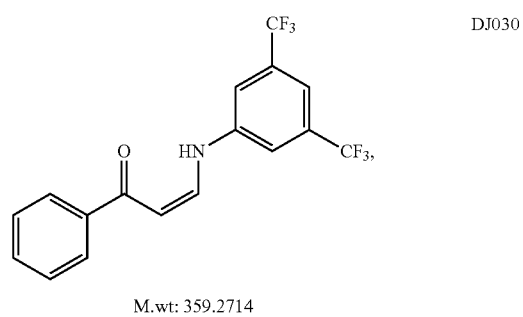
M.wt: 359.2714 — DJ030

TABLE 1-continued
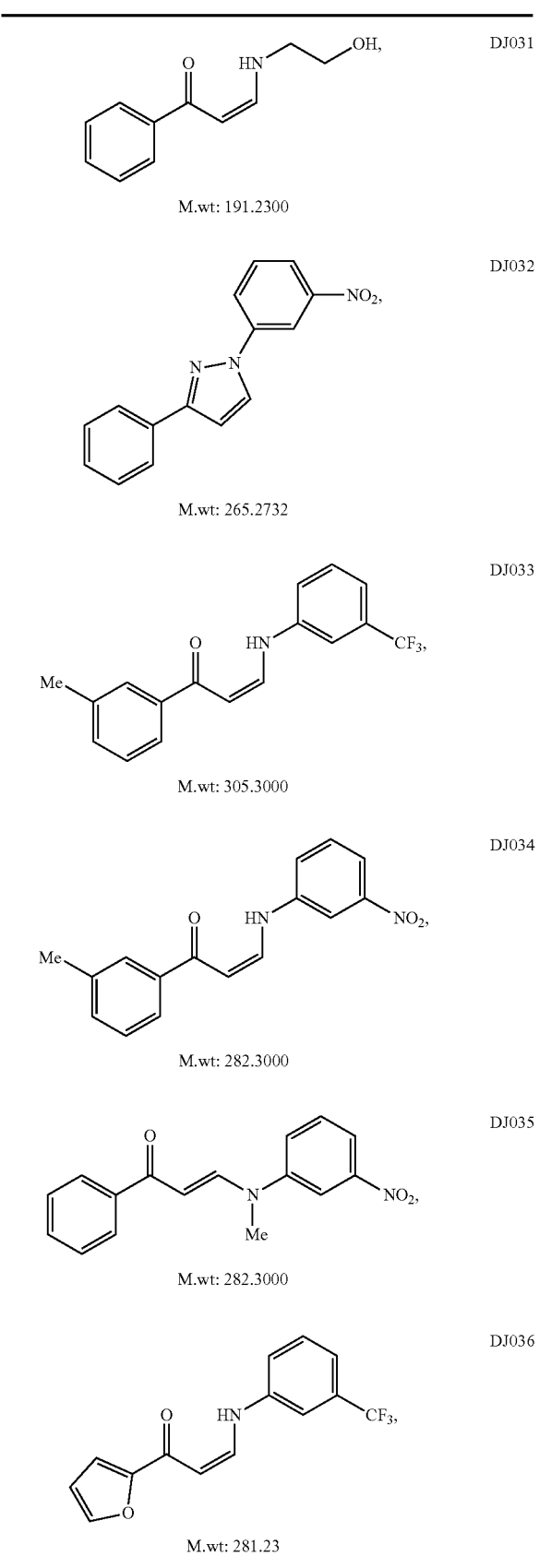
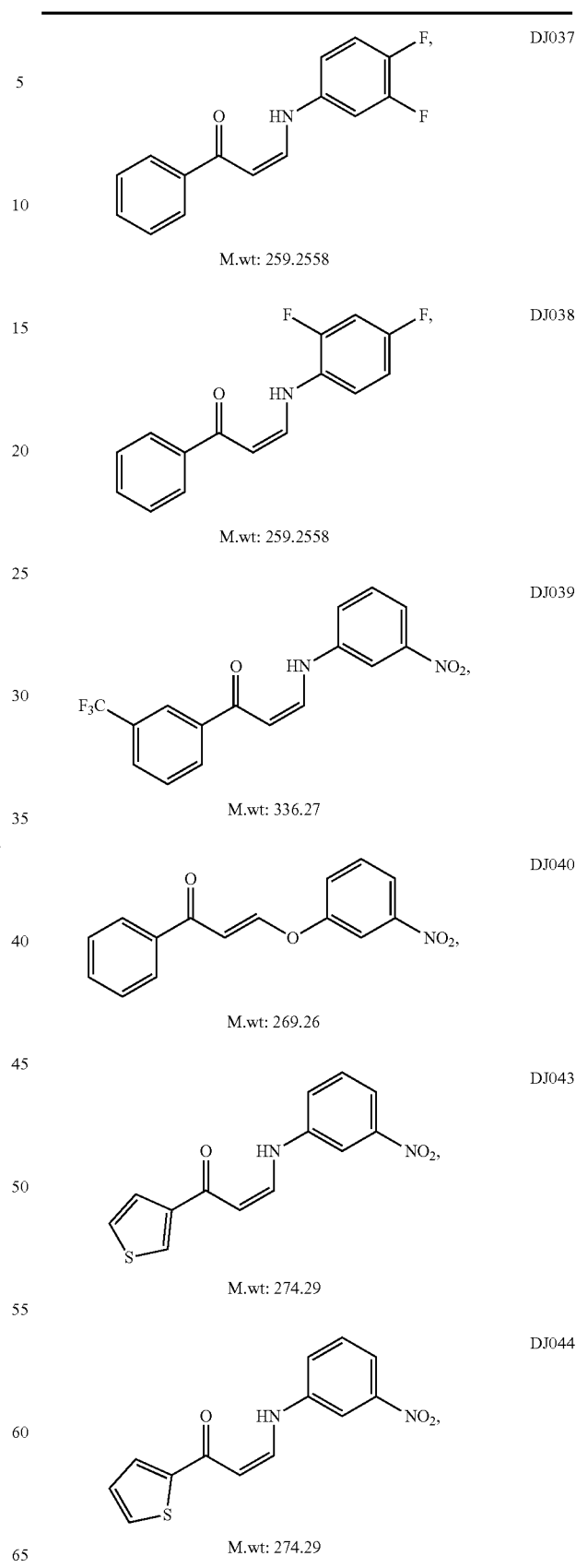

TABLE 1-continued
DJ045
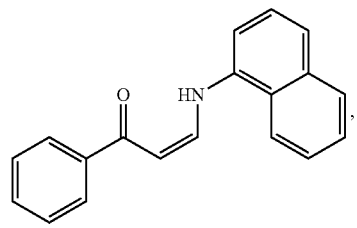
M.wt: 273.34
DJ046
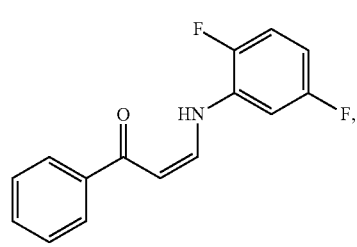
M.wt: 259.2558
DJ047
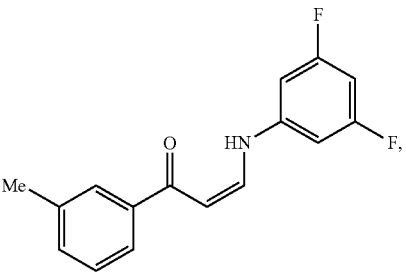
M.wt: 273.28
DJ048
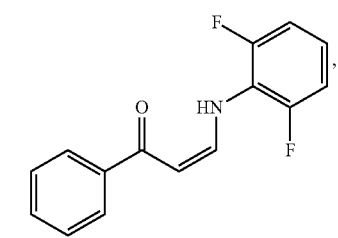
M.wt: 259.2558
DJ049
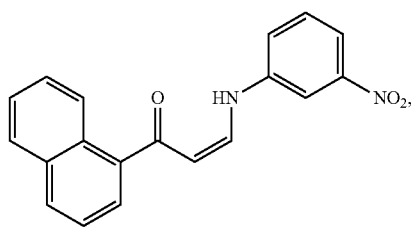
M.wt: 318.33
TABLE 1-continued
DJ050
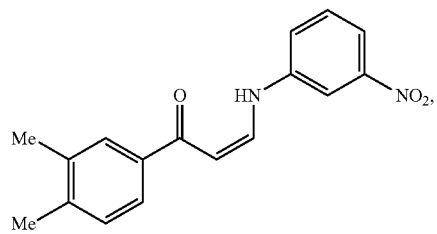
M.wt: 296.33
DJ052
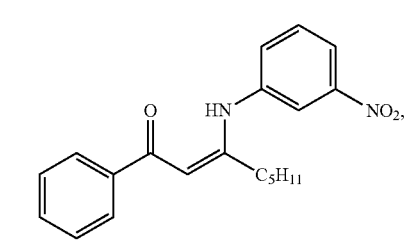
M.wt: 338.41
DJ053
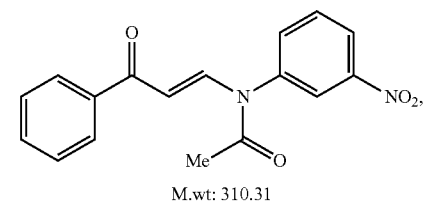 [SMILES: CC(=O)N(/C=C/C(=O)c1ccccc1)c1cccc([N+](=O)[O-])c1]
M.wt: 310.31
DJ055
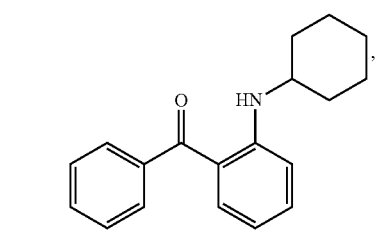
M.wt: 279.38
DJ056
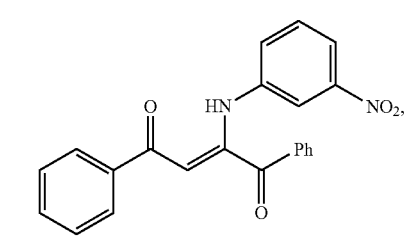
M.wt: 372.38
DJ057
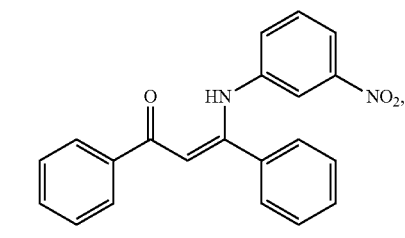
M.wt: 344.37

TABLE 1-continued
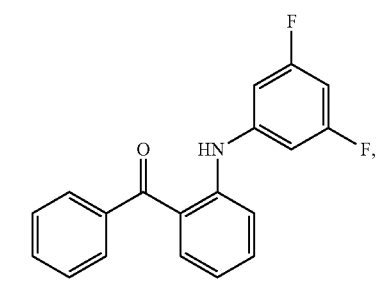
DJ058
M.wt: 309.32
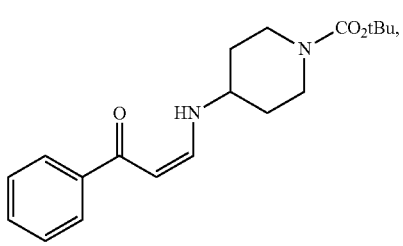
DJ059
M.wt: 330.43
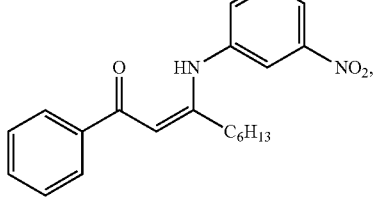
DJ060
M.wt: 352.43
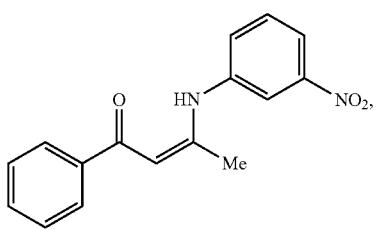
DJ061
M.wt: 282.30
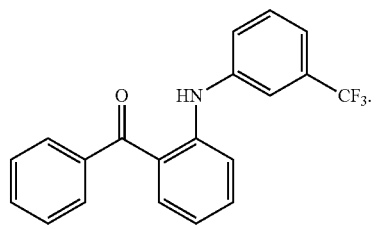
DJ062
M.wt: 341.33
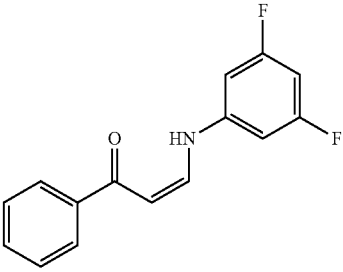
DJ009
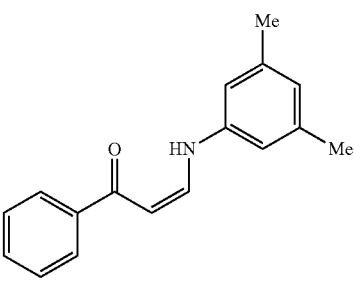
DJ011
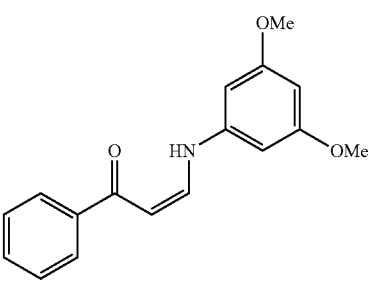
DJ012
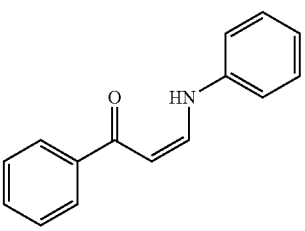
DJ013
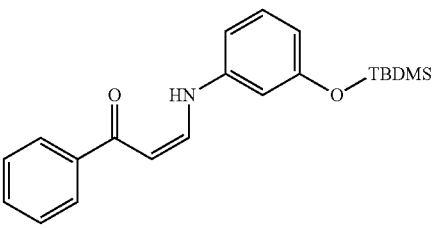
DJ014
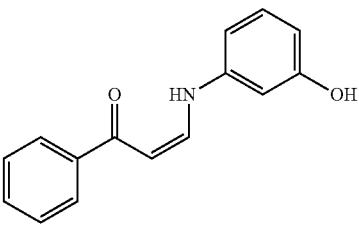
DJ015
and pharmaceutically acceptable salts and/or prodrugs thereof
In certain embodiments, compounds of Formula (I) are selected from:
In certain embodiments, compounds of Formula (III) are selected from compounds DJ028, DJ029, and DJ032.

Certain compounds of the invention are prone to E/Z isomerization in solution and typically exist as a mixture of E and Z isomers. Certain embodiments of the invention are not prone to isomerization in solution. In certain embodiments, compounds of the invention may be enriched in either the E or Z isomer. For example, a compound of the invention may have greater than 50%, 60%, 70%, 80%, 90%, or 95% or more of the E or Z isomer. Those compounds that isomerize in solution in certain solvents may still be prepared in isomerically enriched form in other solvents, or in solid form.

In certain embodiments, compounds of the invention are prodrugs of the compounds described herein. For example, wherein a hydroxyl in the parent compound is presented as an ester or a carbonate, or a carboxylic acid present in the parent compound is presented as an ester. In certain such embodiments, the prodrug is metabolized to the active parent compound in vivo (e.g., the ester is hydrolyzed to the corresponding hydroxyl or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomers. For example, a compound of the invention may have greater than 30% de, 40% de, 50% de, 60% de, 70% de, 80% de, 90% de, or even 95% or greater de.

In certain embodiments, the present invention provides pharmaceutical compositions comprising one or more of the compounds of the present invention. In certain embodiments, the pharmaceutical compositions further comprise a pharmaceutically acceptable excipient.

In certain embodiments, the present invention relates to methods of treatment with a compound selected from Table 1, or a pharmaceutically acceptable salt thereof. In certain embodiments, the therapeutic preparation may be enriched to provide predominantly one enantiomer or isomer of a compound (e.g., of a compound selected from Table 1). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of a compound selected from Table 1). A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound selected from Table 1, or a pharmaceutically acceptable salt thereof. In certain embodiments, the therapeutic preparation may be enriched to provide predominantly one enantiomer of a compound (e.g., of a compound selected from Table 1). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of a compound selected from Table 1). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention, such as a compound selected from Table 1), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

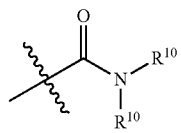

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

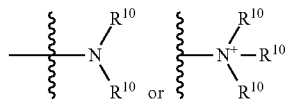

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

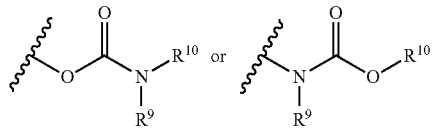

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —C(O)O$R^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms.

Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "silyloxy" refers to an oxygen moiety with a silyl attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO3H, or a pharmaceutically acceptable salt thereof.

The term "sulfonamide" is art-recognized and refers to the group represented by the general formulae

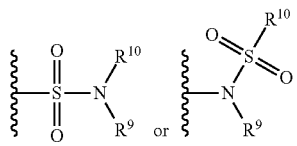

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

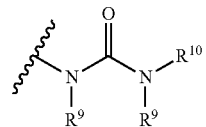

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. For example, a compound that prevents epilepsy may reduce the frequency of seizures and/or reduce the severity of seizures.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention (e.g., a compound selected from Table 1). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds selected from Table 1 in a formulation represented above can be replaced with the corresponding suitable prodrug, e.g., wherein a hydroxyl in the parent compound is presented as an ester or a carbonate or carboxylic acid present in the parent compound is presented as an ester.

The term "myelosuppressive" refers to therapies, treatments, or other actions taken on a subject that have the effect of decreasing the production of leukocytes, erythrocytes, and/or thrombocytes in that subject. The term "myelosuppressed" refers to a subject whose production of leukocytes, erythrocytes, and/or thrombocytes has been decreased below the normal level in that subject.

The terms "agonist", "antagonist", and "inhibitor" are used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal cells or tissues. They include, for example, agents whose structure is known, and those whose structure is not known. An agonist refers to an agent that increases the activity of a protein. For example, a Rac1 agonist may increase the amount of Rac1-GTP in a cell. The terms "antagonist" and "inhibitor" are used interchangeably herein. An inhibitor may, for example, reduce the phosphatase activity of PTPσ. The inhibitor may inhibit a target such as PTPσ by reducing the amount of translation of a PTPσ mRNA, e.g., the inhibitor may be an interfering nucleic acid. Similarly, an inhibitor may reduce the phosphatase activity of PTPσ by, for example, binding to a conformation of PTPσ that has reduced phosphatase activity.

Populations of Cells

In some aspects, the invention relates to a population of mammalian cells comprising hematopoietic stem cells ("HSCs"), wherein the population is substantially free of cells that express protein tyrosine phosphatase sigma ("PTPσ"). The population may further comprise an inhibitor of the PTPσ pathway.

The term "substantially free of cells that express", such as in a "population of cells that is substantially free of cells that express PTPσ", may refer to compositions in which cells that express a high level of the molecule have been substantially removed and cells that express a low level of the molecule remain. The skilled artisan will recognize that a population of cells that is substantially free of cells that express PTPσ may comprise cells that express a detectable amount of PTPσ. Further, the skilled artisan will recognize that the threshold for distinguishing cells that express a high level of a molecule from cells that express a low level of a molecule may vary according to the overall context in which the distinction is being made. When two discrete populations of cell cannot be identified, the term "substantially free of cells that express [a molecule]" refers to the selection of cells that express low levels of the molecule. For example, FIG. 1D shows various flow cytometry gates that do not distinguish two discrete populations of cells. In this case, the term substantially free of cells that express PTPσ refers to cells that are gated as low-expressing cells. A population of cells that is substantially free of cells that express PTPσ may therefore be obtained, for example, by collecting the gated cells. The placement of the gate may be arbitrary. Thus, the population of cells that is substantially free of cells that express PTPσ may be generated, for example, by gating a population of cells that comprises less than 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, or 25% of the cells in a sample, wherein the gated cells were determined to express the least amount PTPσ. Similarly, the population of cells that is substantially free of cells that express PTPσ may be generated, for example, by removing at least 10%, 15%, 20%, 25%, 30%, 35%, 40%, 45%, 50%, 55%, 60%, 65%, or 70% of the cells that express the most PTPσ from the sample. Those with skill in the art will know that the gate may be adjusted based on other gates, for example, based on gates that select for other characteristics of HSCs.

In some embodiments, the invention relates to a population of mammalian cells comprising HSCs, wherein the population is enriched in PTPσ⁻ cells. The population may further comprise an inhibitor of the PTPσ pathway.

The term "enriched" refers to a population that has been processed to either collect cells that possess the enriched characteristic or to remove cells that do not possess the characteristic. The skilled artisan will recognize that a characteristic such as PTPσ⁻ or PTPσ⁺ may be arbitrarily defined. As described herein, PTPσ⁺ cells express more PTPσ on average than PTPσ⁻ cells, such as during the sorting of a population of cells. A population is enriched in PTPσ⁻ cells if the population is obtained by preferentially collecting cells that express low levels of PTPσ relative to cells that express higher levels of PTPσ, for example by FACS or MACS. Similarly, a population is enriched in PTPσ⁻ cells if the population is obtained by preferentially removing cells that express high levels of PTPσ relative to cells that express lower levels of PTPσ.

In some aspects, the invention relates to a population of mammalian cells comprising HSCs and an inhibitor of the PTPσ pathway.

In some embodiments, the invention relates to a cell population, wherein the population is enriched in $CD34^+$, $CD38^-$, $CD45RA^-$, $CD90^+$, $lin^-$, $Rho^{lo}$, $CD49f^{+-}$, and/or $CD33^-$ cells. The population may be enriched, for example, in $CD34^+CD38^-CD45RA^-Lin^-$ cells or $CD34^+CD38^-CD45RA^-Lin^-PTP\sigma^-$ cells. Similarly, in some embodiments, the invention relates to a cell population, wherein the population is substantially free of $CD34^-$, $CD38^+$, $CD45RA^+$, $CD90^-$, $lin^+$, $Rho^{hi}$, $CD49f^-$, and/or $CD33^+$ cells. The HSCs of the invention may be, for example, mice or human HSCs. In some embodiments, the HSCs are cord blood or bone marrow HSCs.

Uses of the Compounds

In certain embodiments, the compounds of the present invention can inhibit PTPσ. In certain embodiments, administration of the compounds of the present invention can cause the rapid recovery of HSCs, hematopoietic reconstitution and improved survival. In certain embodiments, administration of the compounds of the present invention promotes the self-renewal or regeneration of hematopoietic stem cells in vivo in mammals, such as humans or mice. In certain embodiments, administration of the compounds of the present invention promotes the self-renewal or regeneration of hematopoietic stem cells in patients that are myelosuppressed. In certain embodiments, administration of the compounds of the present invention promote the self-renewal or regeneration of hematopoietic stem cells in patients receiving myelosuppressive therapy, such as chemo- or radiotherapy, patients undergoing hematopoietic cell transplantation and patients with aplastic anemia and degenerative hematologic diseases.

In certain embodiments, the present invention provides methods of inhibiting PTPσ using a compound or composition of the present invention. In certain embodiments, the present invention provides methods of promoting rapid recovery of HSCs, hematopoietic reconstitution and improved survival. In certain embodiments, the present invention provides methods of promoting the self-renewal or regeneration of hematopoietic stem cells in vivo in mammals, such as humans or mice, by administering a therapeutically effective amount of compound or composition of the present invention. In certain embodiments, the present invention provides methods of promoting self-renewal or regeneration of hematopoietic stem cells in patients that are myelosuppressed. In certain embodiments, the present invention provides methods of promoting the self-renewal or regeneration of hematopoietic stem cells in patients receiving myelosuppressive therapy, such as chemo- or radiotherapy, patients undergoing hematopoietic cell transplantation and patients with aplastic anemia and degenerative hematologic diseases.

In some embodiments, the invention relates to methods for promoting hematopoietic reconstitution in a subject in need thereof, the method comprising administering to the subject an inhibitor of a PTPσ pathway. The subject may have received an implant comprising hematopoietic cells, such as a transplant comprising hematopoietic cells. For example, the subject may require an allogeneic bone marrow transplantation. In some embodiments, the implant is a cord blood or bone marrow implant. In some embodiments, the method further comprises administering hematopoietic cells to the patient, e.g., before the subject receives the implant, simultaneously with the implant, and/or after the subject receives the implant.

In some embodiments, the subject has compromised hematopoietic function. For example, the compounds of the present invention may be administered to accelerate the subject's own hematopoietic reconstitution process.

In some embodiments, the compounds of the present invention are administered systemically. The inhibitor may accelerate hematologic recovery.

The subject may need hematopoietic reconstitution to counteract the effects of myelosuppressive therapy, e.g., because the subject has received myelosuppressive therapy. In some embodiments, the myelosuppressive therapy is chemotherapy. In some embodiments, the subject is a chemotherapy patient and the inhibitor is administered prior to administering the chemotherapy. In some embodiments, the subject is a chemotherapy patient and the inhibitor is administered concurrently with the chemotherapy. In some embodiments, the subject is a chemotherapy patient and the inhibitor is administered after administering the chemotherapy.

In other embodiments, the myelosuppressive therapy is radiation. In some embodiments, the inhibitor is administered prior to administering a radiation treatment. In some embodiments, the inhibitor is administered concurrently with radiation treatment. In some embodiments, the inhibitor is administered after administering radiation treatment.

In some embodiments, the subject has been exposed to radiation.

In some embodiments, the subject is a mammal. For example, the subject may be a mouse or a human.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition.

The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals.

A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Example 1: Synthetic Protocols

DJ001 (also identified as UCLA 5483071) and its analogues were prepared by either of two simple methods. Heating the readily available aryl 2-chloroenone 1001 or the aryl enynone 1002 with any of several aryl amines gave the desired aryl 2-arylamino enones:

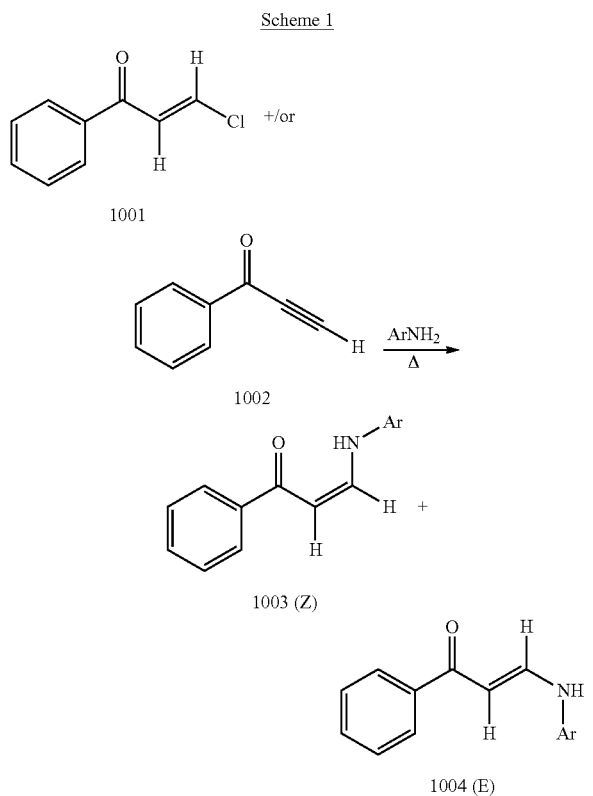

Procedures for the Synthesis of Ketones 1001 and 1002

The acetylenic ketones were synthesized according to a literature procedure (*Helv. Chim. Acta* 1979, 62, 852; *Org. Lett.* 2012, 14 (22), 5756; *Org. Lett.* 2011, 13 (17), 4680; *Chem. Eur. J.* 2014, 20 (35), 11101; *Synth. Commun.* 2010, 40, 1280).

The β-E-chlorovinylketones were synthesized according to a literature procedure (*Chim. Acta Turcica* 1990, 18, 125 and *Gazz. Chim. Ital.* 1947, 77, 549).

General Procedure A for the Synthesis of Compounds DJ (DJ001-DJ009, DJ011, DJ013-DJ016)

The aniline (1.2-1.5 equiv.) dissolved in pyridine was added to the chlorovinylketone 1001 and the reaction mixture was stirred at 65° C. for 2 hours. The reaction mixture was concentrated under reduced pressure. The remaining residue was purified by column chromatography on silica gel (Hexanes/EtOAc).

DJ015 was synthesized according to procedure A followed by deprotection according to the literature (*Org. Lett.* 2015, 17 (10), 2298).

General Procedure B for the Synthesis of Compounds DJ Starting from the Acetylenic Ketones (DJ012, DJ030)

A mixture of the acetylenic ketone 1002, the aniline (1.5 equiv.), and copper iodide (20-40 mol %) in DMF/H$_2$O was stirred under argon at 85° C. for 20 hours. After cooling down to room temperature, the reaction mixture was diluted with H$_2$O and extracted with EtOAc. The gathered organic phases were washed with NH$_4$Cl/NH$_3$ (v/v: 1/1), brine, dried over MgSO$_4$, filtered and concentrated under reduced pressure. The remaining residue was purified by column chromatography on silica gel (Hexanes/EtOAc).

General Procedure C for the Synthesis of Compounds DJ Starting from the Acetylenic Ketones (DJ017-DJ026, DJ031)

The amine (1.5 equiv.) was added to a solution of the acetylenic ketone 1002 in PhMe and the reaction mixture was stirred at room temperature or 80° C. (DJ020) overnight. The reaction mixture was concentrated under reduced pressure. The remaining residue was purified by column chromatography on silica gel (Hexanes/EtOAc).

DJ031 was synthesized according to procedure C followed by deprotection according to the literature (*Org. Lett.* 2015, 17 (10), 2298).

General Procedure D for the Synthesis of Compounds DJ Starting from Acetophenone (DJ028, DJ029, DJ032)

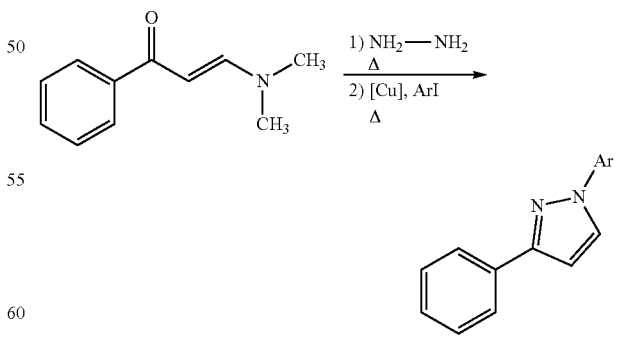

A mixture of acetophenone and dimethylformamide dimethylacetal (2.0 equiv.) was refluxed overnight. The reaction mixture was allowed to cool down to room temperature and was concentrated under reduced pressure. The remaining residue was suspended in hexanes and filtered. The filter cake was washed with plenty of hexanes. (E)-3-(dimethylamino)-1-phenylprop-2-en-1-one was obtained.

Hydrazine-monohydrate (5.0 equiv.) was added to a solution of (E)-3-(dimethylamino)-1-phenylprop-2-en-1-one in EtOH and the resulting reaction mixture was refluxed for 2 hours. The reaction was then allowed to cool down to room temperature and was concentrated under reduced pressure. The remaining residue was diluted with $H_2O$ and extracted with $CH_2Cl_2$. The organic phase was dried over $MgSO_4$, filtered and concentrated under reduced pressure. The residue was considered pure enough by $^1$H-NMR (>95%) to be used without further purification.

A mixture of phenylpyrazole, iodoarene (1.0 equiv.), copper iodide (20 mol %), trans-1,2-diaminocyclohexane (25 mol %), potassium carbonate (2.0 equiv.) in dioxane was stirred at 100° C. under argon for 16 hours. After cooling down to room temperature, the reaction mixture was diluted with $H_2O$ and extracted with EtOAC. The gathered organic phases were washed with $NH_4Cl/NH_3$ (v/v: 1/1), brine, dried over $MgSO_4$, filtered and concentrated under reduced pressure. The remaining residue was purified by column chromatography on silica gel (Hexanes/EtOAc).

General Procedure E for the Synthesis of Compounds DJ Starting from 2-Aminobenzophenone and Iodoarene (DJ027, DJ058, and DJ062)

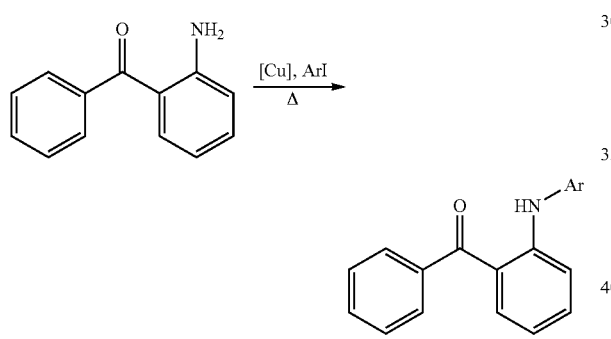

A mixture of 2-aminobenzophenone, iodoarene (1.5 equiv.), copper (1.5 equiv.), 18-Crown-6 (15 mol %), potassium carbonate (1.5 equiv.) in DMF was stirred under argon at 120° C. for 24 hours. After cooling down to room temperature, the reaction mixture was diluted with $H_2O$ and extracted with EtOAc. The gathered organic phases were washed with $NH_4Cl/NH_3$ (v/v: 1/1), brine, dried over $MgSO_4$, filtered and concentrated under reduced pressure. The remaining residue was purified by column chromatography on silica gel (Hexanes/EtOAc).

General Procedure F for the Synthesis of Compounds DJ Starting from 2-Aminobenzophenone and Cycloalkanone (DJ055)

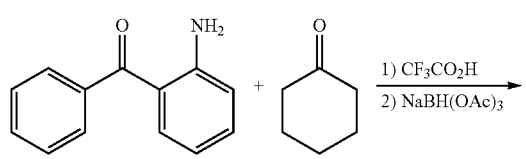

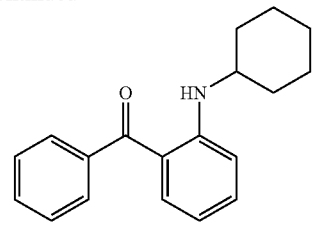

Trifluoroacetic acid (1.5 equiv.) was added to a solution of 2-aminobenzophenone and cyclohexanone (1.1 equiv.) in 1,2-dichloroethane (2 mL) at 0° C. and stirred at the same temperature for one hour. Sodium triacetoxyborohydride (2.2 equiv.) was then added in one portion and the reaction mixture was allowed to warm up to room temperature and was stirred overnight. The reaction mixture was quenched with saturated aqueous $NaHCO_3$(100 mL), extracted with $CH_2Cl_2$ (3×50 mL). The gathered organic phases were washed brine (50 mL), dried over $Na_2SO_4$, filtered and concentrated under reduced pressure. The remaining residue was purified by column chromatography on silica gel (Hexanes/EtOAc).

General Procedure G for the Synthesis of Compounds DJ Starting from 1005 and $ArNH_2$ (DJ052, DJ060, DJ057)

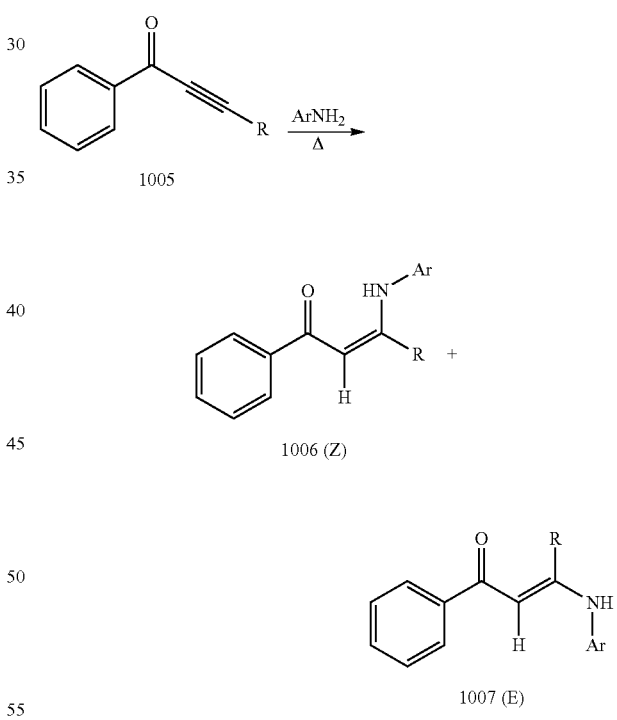

A solution of 1005 and aniline (2.5 equiv.) was refluxed for 72 hours, while being monitored by thin layer chromatography. The reaction mixture was allowed to cool down to room temperature and was concentrated under reduced pressure. The remaining residue was purified by column chromatography on silica gel (Hexanes/EtOAc).

Other Synthetic Procedures

DJ010 was prepared by heating the readily available acetophenone and dimethylformamide dimethylacetal (DMF-DMA).

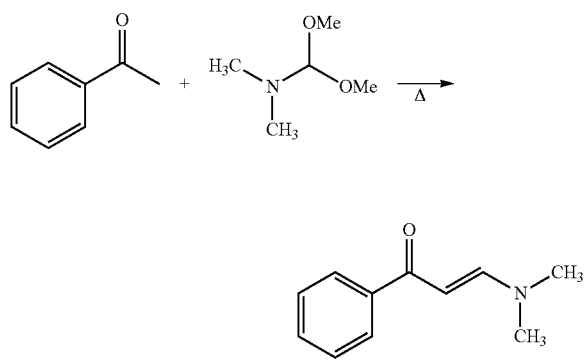

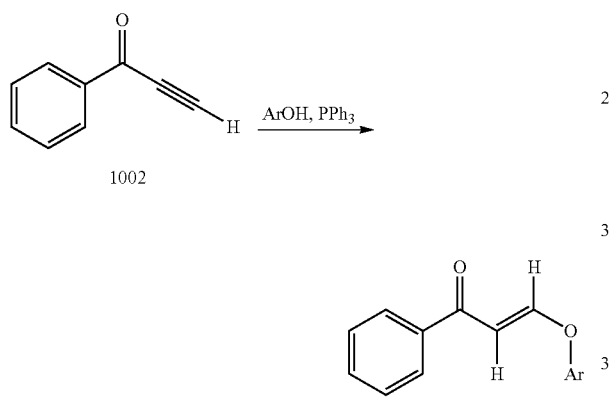

DJ040 was prepared by reacting the readily available aryl enynone 1002 with a phenol in the presence of triphenylphosphine at room temperature.

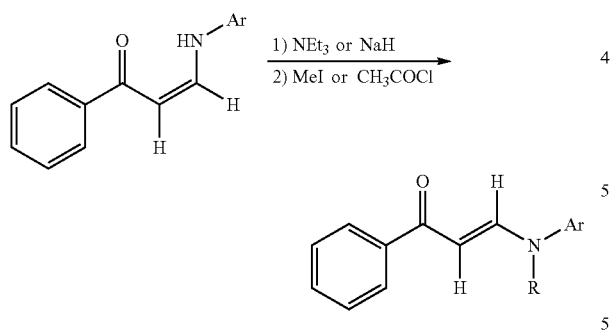

DJ035 and DJ053 were prepared by reacting DJ001 with triethylamine or NaH, followed by addition of iodomethane or acetyl chloride.

The compounds DJ001-DJ019, and other compounds capable of forming internal hydrogen bonds, were formed as the Z-isomer shown. However, when the compounds were dissolved in solvents such as DMSO, the pure Z-isomer was converted quickly to a roughly 1:1 mixture of the Z- and E-isomers.

NMR Data

The identity of compounds synthesized according to the methods described above was confirmed by NMR spectroscopy. Exemplary spectroscopic data is listed below.

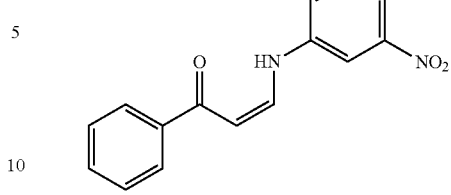

$^1$H NMR (CDCl$_3$, 400 MHz) δ (ppm): 12.25 (d, J=11.3 Hz, 1H), 7.98-7.93 (m, 3H), 7.91 (ddd, J=8.1, 2.1, 0.9 Hz, 1H), 7.56-7.45 (m, 5H), 7.37 (ddd, J=8.2, 2.4, 0.9 Hz, 1H), 6.16 (d, J=8.4 Hz, 1H). $^{13}$C NMR (CDCl$_3$, 100 MHz) δ (ppm): 191.8, 149.4, 143.4, 141.7, 138.6, 132.2, 130.6, 128.6, 127.5, 122.3, 117.8, 110.0, 95.7.

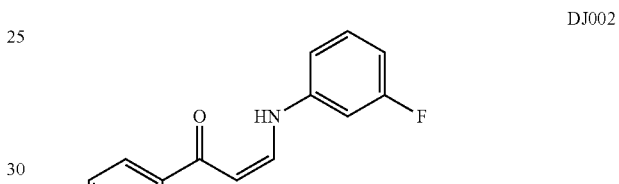

$^1$H NMR (CDCl$_3$, 400 MHz) δ (ppm): 12.11 (d, J=10.7 Hz, 1H), 7.94 (dt, J=8.5, 1.2 Hz, 2H), 7.53-7.43 (m, 4H), 7.32-7.26 (m, 1H), 6.87 (dd, J=8.1, 1.5 Hz, 1H), 6.82 (dt, J=10.4, 2.2 Hz, 1H), 6.77 (tdd, J=8.3, 2.4, 0.1 Hz, 1H), 6.02 (d, J=7.7 Hz, 1H). $^{13}$C NMR (CDCl$_3$, 100 MHz) δ (ppm): 191.4, 163.8 (d, J=246 Hz), 144.2, 142.0 (d, J=10.2 Hz), 138.9, 131.8, 131.1 (d, J=5.7 Hz), 128.5, 127.4, 112.1 (d, J=2.8 Hz), 110.2 (d, J=21.3 Hz), 103.3 (d, J=25.4 Hz), 94.5.

$^{19}$F NMR (CDCl$_3$, 376 MHz) δ (ppm): −110.

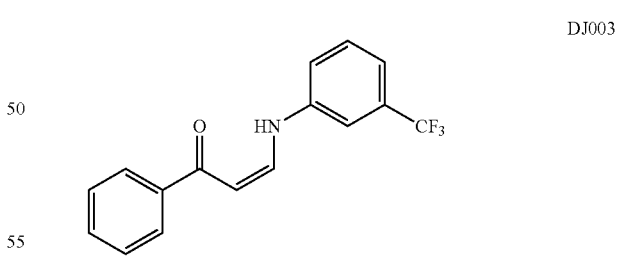

$^1$H NMR (CDCl$_3$, 400 MHz) δ (ppm): 12.33 (d, J=12.5 Hz, 1H), 7.95 (dt, J=9.7, 0.2 Hz, 2H), 7.54-7.44 (m, 5H), 7.34-7.30 (m, 2H), 7.25 (dd, J=7.9, 1.9 Hz, 1H), 6.06 (d, J=7.8 Hz, 1H).

$^{13}$C NMR (CDCl$_3$, 100 MHz) δ (ppm): 191.5, 144.0, 140.9, 138.9, 132.3 (q, J=33 Hz), 131.9, 130.4, 128.5, 127.4, 123.8 (q, J=272 Hz), 119.9 (q, J=3.7 Hz), 119.5, 112.6 (q, J=3.8 Hz), 94.9.

$^{19}$F NMR (CDCl$_3$, 376 MHz) δ (ppm): −62.9.

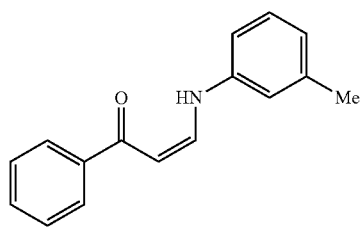

DJ004

¹H NMR (CDCl₃, 400 MHz) δ (ppm): 12.1 (d, J=11.6 Hz, 1H), 7.94 (dt, J=6.7, 1.4 Hz, 2H), 7.55-7.43 (m, 4H), 7.23 (t, J=7.8 Hz, 1H), 6.93-6.89 (m, 3H), 6.01 (d, J=7.9 Hz, 1H), 2.36 (s, 3H).

¹³C NMR (CDCl₃, 100 MHz) δ (ppm): 190.9, 145.1, 140.2, 139.8, 139.3, 131.5, 129.6, 128.4, 127.3, 124.6, 117.2, 113.5, 93.6, 21.5.

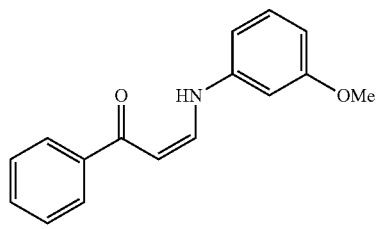

DJ005

¹H NMR (CDCl₃, 400 MHz) δ (ppm): 12.1 (d, J=11.6 Hz, 1H), 7.94 (dt, J=9.6, 1.2 Hz, 2H), 7.53-7.43 (m, 4H), 7.26-7.23 (m, 1H), 6.71 (dt, J=1.3, 0.2 Hz, 1H), 6.64-6.62 (m, 2H), 6.51 (d, J=6.5 Hz, 1H), 3.82 (s, 3H).

¹³C NMR (CDCl₃, 100 MHz) δ (ppm): 190.0, 160.9, 144.9, 144.5, 139.2, 131.6, 130.6, 128.5, 127.3, 109.2, 108.7, 102.4, 93.8, 55.4.

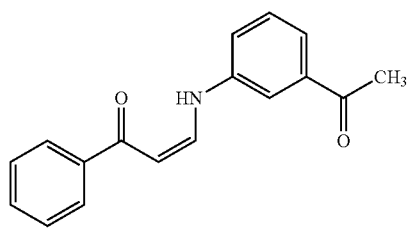

DJ006

¹H NMR (CDCl₃, 400 MHz) δ (ppm): 12.2 (d, J=12.1 Hz, 1H), 7.95 (dt, J=6.9, 1.2 Hz, 2H), 7.73 (t, J=2.1 Hz, 1H), 7.64 (dt, J=7.8, 1.2 Hz, 1H), 7.58 (dd, J=12.1, 7.9 Hz, 1H), 7.54-7.50 (m, 1H), 7.47-7.43 (m, 3H), 7.28 (tdd, J=8.5, 2.5, 0.8 Hz, 1H), 6.09 (d, J=7.9 Hz, 1H), 2.62 (s, 3H).

¹³C NMR (CDCl₃, 100 MHz) δ (ppm): 197.5, 191.4, 144.4, 140.8, 138.6, 138.5, 131.8, 130.0, 128.5, 127.4, 123.5, 121.0, 115.0, 94.6, 26.7.

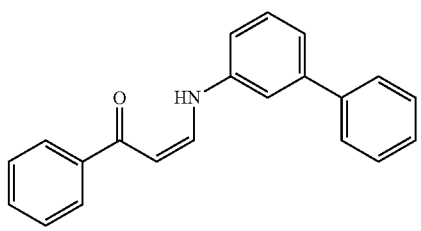

DJ007

¹H NMR (CDCl₃, 400 MHz) δ (ppm): 12.2 (d, J=12.4 Hz, 1H), 7.95 (dt, J=6.7, 1.3 Hz, 2H), 7.62-7.58 (m, 3H), 7.53-7.44 (m, 5H), 7.42-7.35 (m, 2H), 7.32-7.29 (m, 2H), 7.10 (ddd, J=8.1, 1.7, 1.5 Hz, 1H), 6.06 (d, J=8.1 Hz, 1H).

¹³C NMR (CDCl₃, 100 MHz) δ (ppm): 190.9, 144.8, 143.0, 140.7, 140.5, 139.2, 131.6, 130.1, 128.9, 128.5, 127.8, 127.4, 127.2, 122.6, 115.3, 115.1, 93.9.

DJ008

¹H NMR (CDCl₃, 400 MHz) δ (ppm): 12.1 (d, J=12.4 Hz, 1H), 7.94 (dt, J=6.5, 1.3 Hz, 2H), 7.55 (dd, J=12.4, 7.9 Hz, 1H), 7.51-7.42 (m, 3H), 7.19 (t, J=8.2 Hz, 1H), 6.51-6.45 (m, 2H), 6.39 (t, J=2.3 Hz, 1H), 6.00 (d, J=7.9 Hz, 1H), 2.97 (s, 6H).

¹³C NMR (CDCl₃, 100 MHz) δ (ppm): 190.8, 151.7, 145.4, 141.1, 139.4, 131.4, 130.2, 128.4, 127.3, 108.2, 103.8, 101.0, 93.2, 40.5.

DJ009

¹H NMR (CDCl₃, 400 MHz) δ (ppm): 12.0 (d, J=11.7 Hz, 1H), 7.94 (dt, J=6.9, 1.6 Hz, 2H), 7.55-7.50 (m, 1), 7.48-7.45 (m, 2H), 7.38 (dd, J=11.7, 8.2 Hz, 1H), 6.64-6.57 (m, 2H), 6.54-6.47 (m, 1H), 6.09 (d, J=8.2 Hz, 1H).

¹³C NMR (CDCl₃, 100 MHz) δ (ppm): 191.7, 164.0 (dd, J=249, 15 Hz), 143.5, 142.8 (t, J=13 Hz), 138.7, 132.1, 128.6, 127.5, 99.3 (d, J=30 Hz), 99.2 (d, J=11 Hz), 98.5 (t, J=26 Hz), 95.3.

¹⁹F NMR (CDCl₃, 376 MHz) δ (ppm): −107.9.

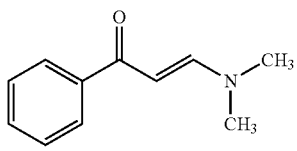
DJ010

¹H NMR (CDCl₃, 400 MHz) δ (ppm): 7.89 (dt, J=6.5, 1.5 Hz, 2H), 7.79 (d, J=12.5 Hz, 1H), 7.46-7.37 (m, 3H), 5.70 (d, J=12.5 Hz, 1H), 3.12 (s, 3H), 2.91 (s, 3H).
¹³C NMR (CDCl₃, 100 MHz) δ (ppm): 188.7, 154.2, 140.6, 130.9, 128.1, 127.7, 127.5, 92.3, 44.9, 37.3.

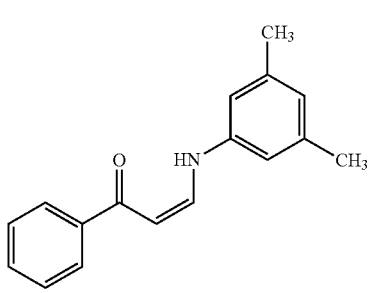
DJ011

¹H NMR (CDCl₃, 400 MHz) δ (ppm): 12.08 (d, J=12.4 Hz, 1H), 7.93 (dt, J=6.7, 1.4 Hz, 2H), 7.54-7.42 (m, 4H), 6.74-6.73 (m, 3H), 5.99 (d, J=7.9 Hz, 1H), 2.31 (s, 6H).
¹³C NMR (CDCl₃, 100 MHz) δ (ppm): 190.8, 145.1, 140.2, 139.6, 139.3, 131.5, 128.4, 127.3, 125.6, 114.3, 93.4, 21.4.

DJ012

¹H NMR (CDCl₃, 400 MHz) δ (ppm): 12.07 (d, J=12.4 Hz, 1H), 7.93 (dt, J=6.8, 1.4 Hz, 2H), 7.52-7.43 (m, 4H), 6.26 (d, J=2.2 Hz, 2H), 6.20 (t, J=2.2 Hz, 1H), 6.01 (d, J=7.8 Hz, 1H), 3.79 (s, 6H).
¹³C NMR (CDCl₃, 100 MHz) δ (ppm): 191.1, 161.9, 144.8, 142.1, 139.2, 131.7, 128.5, 127.3, 95.8, 95.0, 93.8, 55.5.

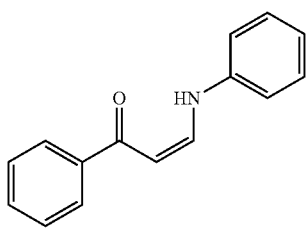
DJ013

¹H NMR (CDCl₃, 400 MHz) δ (ppm): 12.15 (d, J=11.5 Hz, 1H), 7.94 (dt, J=6.6, 1.2 Hz, 2H), 7.53 (dd, J=12.3, 7.8 Hz, 1H), 7.52-7.43 (m, 3H), 7.35 (t, J=8.2 Hz, 2H), 7.15-7.06 (m, 3H), 6.03 (d, J=7.7 Hz, 1H).
¹³C NMR (CDCl₃, 100 MHz) δ (ppm): 190.9, 145.0, 140.3, 139.2, 131.6, 129.8, 128.5, 127.3, 123.7, 116.4, 93.7.

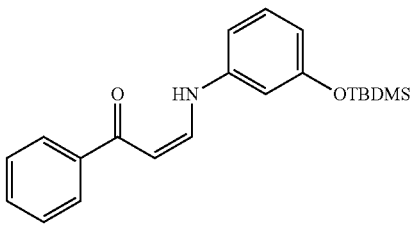
DJ014

¹H NMR (CDCl₃, 400 MHz) δ (ppm): 12.05 (d, J=12.9 Hz, 1H), 7.93 (dt, J=6.7, 1.4 Hz, 2H), 7.52-7.43 (m, 4H), 7.18 (t, J=8.1 Hz, 1H), 6.71 (dd, J=8.1, 2.1 Hz, 1H), 6.59-6.55 (m, 2H), 6.02 (d, J=7.9 Hz, 1H), 0.99 (s, 9H), 0.22 (s, 6H).
¹³C NMR (CDCl₃, 100 MHz) δ (ppm): 191.0, 157.0, 144.9, 141.5, 139.2, 131.6, 130.5, 128.5, 127.3, 115.5, 109.4, 108.5, 93.7, 25.7, 18.2, −4.4.

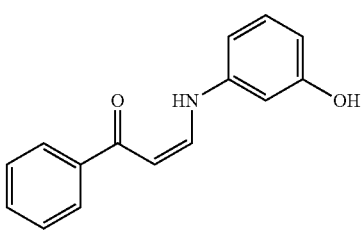
DJ015

¹H NMR (CDCl₃, 400 MHz) δ (ppm): 12.05 (d, J=11.9 Hz, 1H), 7.93 (dt, J=6.9, 1.4 Hz, 2H), 7.53-7.43 (m, 4H), 7.19 (t, J=8.2 Hz, 1H), 6.68 (dd, J=8.1, 2.2 Hz, 1H), 6.64 (t, J=2.2 Hz, 1H), 6.56 (ddd, J=8.2, 2.3, 0.9 Hz, 1H), 6.02 (d, J=7.9 Hz, 1H), 5.62 (br s, 1H).
¹³C NMR (CDCl₃, 100 MHz) δ (ppm): 191.1, 157.2, 145.1, 139.3, 131.7, 130.8, 128.5, 127.4, 111.0, 109.7, 108.7, 103.7, 93.9.

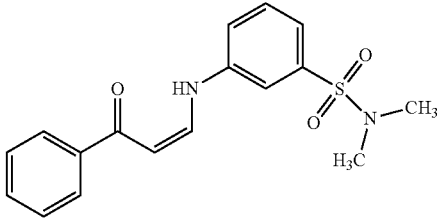
DJ016

¹H NMR (CDCl₃, 400 MHz) δ (ppm): 12.2 (d, J=11.9 Hz, 1H), 7.95 (dt, J=7.0, 1.9 Hz, 2H), 7.55-7.43 (m, 7H), 7.30 (ddd, J=8.0, 2.4, 1.0 Hz, 1H), 6.13 (d, J=8.0 Hz, 1H), 2.77 (s, 6H).
¹³C NMR (CDCl₃, 100 MHz) δ (ppm): 191.7, 143.8, 141.2, 138.8, 137.5, 132.0, 130.5, 128.6, 127.5, 122.1, 120.3, 114.6, 95.3, 38.0.

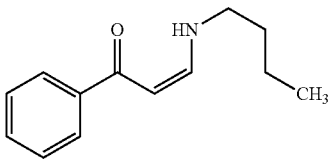

DJ017

¹H NMR (CDCl₃, 400 MHz) δ (ppm): 10.39 (br s, 1H), 7.87 (dd, J=8.0, 1.5 Hz, 2H), 7.45-7.37 (m, 3H), 6.94 (dd, J=12.9, 7.4 Hz, 1H), 5.68 (d, J=7.5 Hz, 1H), 3.27 (q, J=6.5 Hz, 2H), 1.59 (qt, J=6.5 Hz, 2H), 1.41 (sext, J=6.7 Hz, 2H), 0.94 (t, J=6.7 Hz, 3H).

¹³C NMR (CDCl₃, 100 MHz) δ (ppm): 189.8, 154.4, 139.9, 130.8, 128.2, 127.0, 89.9, 49.0, 33.1, 19.8, 13.7.

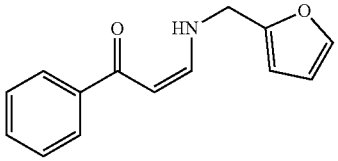

DJ018

¹H NMR (CDCl₃, 400 MHz) δ (ppm): 10.42 (br s, 1H), 7.87 (dt, J=6.5, 1.4 Hz, 2H), 7.47-7.38 (m, 4H), 7.00 (dd, J=12.6, 7.6 Hz, 1H), 6.33 (dd, J=3.2, 1.9 Hz, 1H), 6.26 (dd, J=3.3, 0.70 Hz, 1H), 5.77 (d, J=7.5 Hz, 1H), 4.40 (d, J=5.9 Hz, 2H).

¹³C NMR (CDCl₃, 100 MHz) δ (ppm): 190.4, 153.6, 150.9, 142.8, 139.6, 131.0, 128.3, 127.1, 110.5, 107.9, 91.2, 45.4.

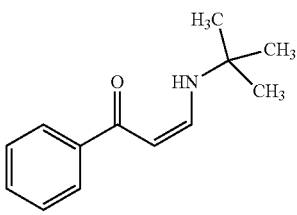

DJ019

¹H NMR (CDCl₃, 400 MHz) δ (ppm): 10.71 (br s, 1H), 7.87 (dd, J=8.0, 1.6 Hz, 2H), 7.42-7.38 (m, 3H), 7.13 (dd, J=13.2, 7.5 Hz, 1H), 5.71 (d, J=7.5 Hz, 1H), 1.35 (s, 9H).

¹³C NMR (CDCl₃, 100 MHz) δ (ppm): 189.5, 149.9, 140.0, 130.7, 128.2, 127.0, 89.9, 52.2, 30.1.

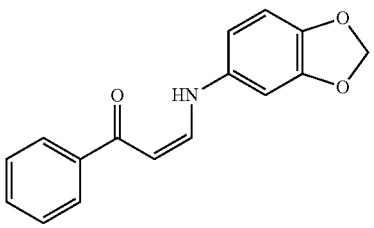

DJ020

¹H NMR (CDCl₃, 400 MHz) δ (ppm): 12.15 (d, J=12.3 Hz, 1H), 7.93 (dt, J=6.7, 1.3 Hz, 2H), 7.49-7.44 (m, 3H), 7.38 (dd, J=12.3, 7.6 Hz, 1H), 6.77 (d, J=7.6 Hz, 1H), 6.66 (d, J=2.2 Hz, 1H), 6.55 (dd, J=8.2, 2.3 Hz, 1H), 5.98 (d, J=8.5 Hz, 1H), 5.97 (s, 2H).

¹³C NMR (CDCl₃, 100 MHz) δ (ppm): 190.7, 148.8, 145.6, 144.3, 139.3, 135.2, 131.5, 128.4, 127.3, 109.7, 108.9, 101.5, 98.6, 93.2.

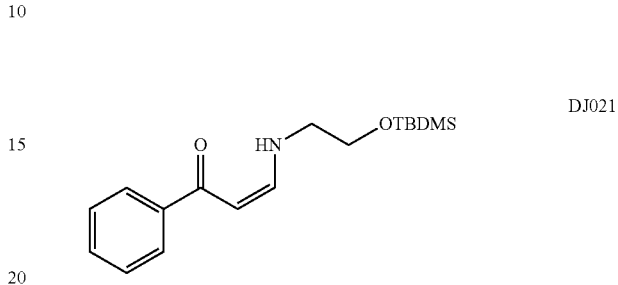

DJ021

¹H NMR (CDCl₃, 400 MHz) δ (ppm): 10.34 (br s, 1H), 7.87 (dt, J=6.3, 1.5 Hz, 2H), 7.44-7.37 (m, 3H), 6.96 (dd, J=12.8, 7.4 Hz, 1H), 5.69 (d, J=7.4 Hz, 1H), 3.73 (t, J=5.4 Hz, 2H), 3.35 (q, J=6.4 Hz, 2H), 0.89 (s, 9H), 0.05 (s, 6H).

¹³C NMR (CDCl₃, 100 MHz) δ (ppm): 190.0, 155.0, 139.9, 130.7, 128.2, 127.1, 90.3, 63.1, 51.2, 25.9, 18.3, −5.4.

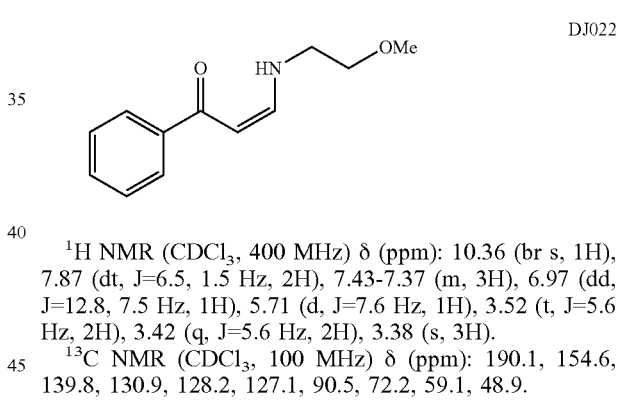

DJ022

¹H NMR (CDCl₃, 400 MHz) δ (ppm): 10.36 (br s, 1H), 7.87 (dt, J=6.5, 1.5 Hz, 2H), 7.43-7.37 (m, 3H), 6.97 (dd, J=12.8, 7.5 Hz, 1H), 5.71 (d, J=7.6 Hz, 1H), 3.52 (t, J=5.6 Hz, 2H), 3.42 (q, J=5.6 Hz, 2H), 3.38 (s, 3H).

¹³C NMR (CDCl₃, 100 MHz) δ (ppm): 190.1, 154.6, 139.8, 130.9, 128.2, 127.1, 90.5, 72.2, 59.1, 48.9.

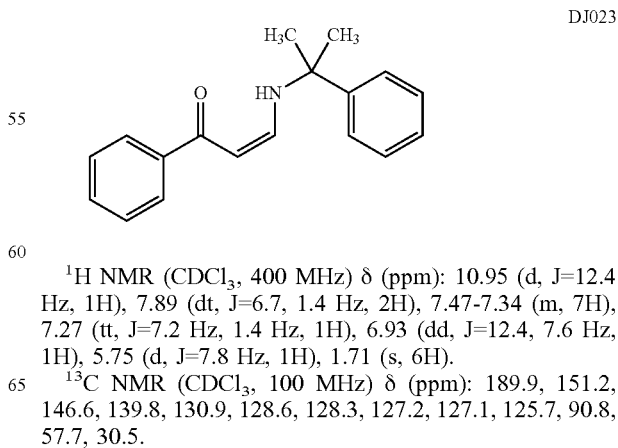

DJ023

¹H NMR (CDCl₃, 400 MHz) δ (ppm): 10.95 (d, J=12.4 Hz, 1H), 7.89 (dt, J=6.7, 1.4 Hz, 2H), 7.47-7.34 (m, 7H), 7.27 (tt, J=7.2 Hz, 1.4 Hz, 1H), 6.93 (dd, J=12.4, 7.6 Hz, 1H), 5.75 (d, J=7.8 Hz, 1H), 1.71 (s, 6H).

¹³C NMR (CDCl₃, 100 MHz) δ (ppm): 189.9, 151.2, 146.6, 139.8, 130.9, 128.6, 128.3, 127.2, 127.1, 125.7, 90.8, 57.7, 30.5.

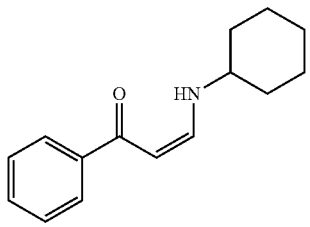
DJ024

¹H NMR (CDCl₃, 400 MHz) δ (ppm): 10.45 (br s, 1H), 7.87 (dt, J=7.6, 1.4 Hz, 2H), 7.45-7.37 (m, 3H), 7.02 (dd, J=13.0, 7.4 Hz, 1H), 5.69 (d, J=7.5 Hz, 1H), 3.17-3.09 (m, 1H), 2.02-1.92 (m, 2H), 1.83-1.75 (m, 2H), 1.46-1.18 (m, 6H).
¹³C NMR (CDCl₃, 100 MHz) δ (ppm): 189.6, 152.3, 139.9, 130.7, 128.2, 127.0, 89.8, 57.4, 34.1, 25.3, 24.6.

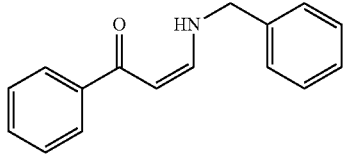
DJ025

¹H NMR (CDCl₃, 400 MHz) δ (ppm): 10.61 (br s, 1H), 7.88 (dt, J=6.5, 1.5 Hz, 2H), 7.47-7.27 (m, 8H), 7.01 (dd, J=12.5, 7.3 Hz, 1H), 5.78 (d, J=7.6 Hz, 1H), 4.46 (d, J=6.1 Hz, 2H).
¹³C NMR (CDCl₃, 100 MHz) δ (ppm): 190.2, 154.1, 139.7, 137.7, 131.0, 128.9, 128.3, 127.8, 127.3, 127.1, 90.9, 52.7.

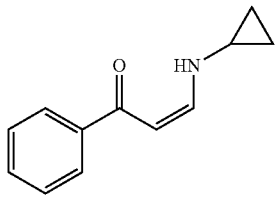
DJ026

¹H NMR (CDCl₃, 400 MHz) δ (ppm): 10.28 (brs, 1H), 7.86 (dt, J=8.0, 1.5 Hz, 2H), 7.44-7.38 (m, 3H), 7.07 (dd, J=12.8, 7.4 Hz, 1H), 5.72 (d, J=7.7 Hz, 1H), 2.84-2.78 (m, 1H), 0.80-0.68 (m, 4H).
¹³C NMR (CDCl₃, 100 MHz) δ (ppm): 190.1, 154.3, 140.2, 131.0, 128.2, 127.1, 90.9, 29.0, 6.5.

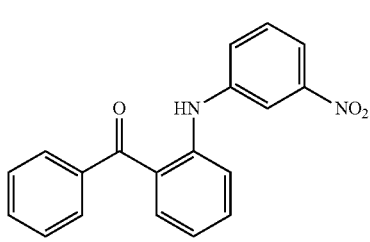
DJ027

¹H NMR (CDCl₃, 400 MHz) δ (ppm): 10.10 (br s, 1H), 8.16 (t, J=2.1 Hz, 1H), 7.85 (ddd, J=7.9, 2.2, 1.3 Hz, 1H), 7.34 (dt, J=7.1, 1.4 Hz, 2H), 7.58 (tt, J=7.5, 1.4 Hz, 2H), 7.53-7.45 (m, 6H), 6.89 (ddd, J=7.8, 6.3, 1.9 Hz, 1H).
¹³C NMR (CDCl₃, 100 MHz) δ (ppm): 199.1, 149.3, 145.5, 142.6, 139.1, 134.9, 134.3, 132.0, 130.2, 129.7, 128.3, 126.3, 121.9, 118.9, 117.1, 115.6, 114.3.

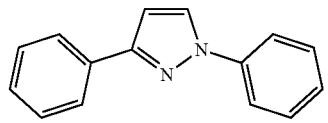
DJ028

¹H NMR (CDCl₃, 400 MHz) δ (ppm): 7.96 (d, J=2.6 Hz, 1H), 7.93-7.90 (m, 2H), 7.79-7.76 (m, 2H), 7.49-7.41 (m, 4H), 7.36-7.26 (m, 2H), 6.78 (d, J=2.6 Hz, 1H).
¹³C NMR (CDCl₃, 100 MHz) δ (ppm): 153.0, 140.3, 133.1, 129.4, 128.7, 128.0, 128.0, 126.3, 125.9, 119.1, 105.0.

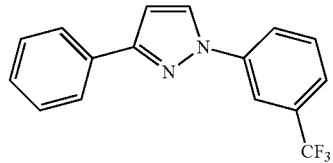
DJ029

¹H NMR (CDCl₃, 400 MHz) δ (ppm): 8.08 (br s, 1H), 8.00 (d, J=2.6 Hz, 1H), 7.98-7.91 (m, 3H), 7.61-7.51 (m, 2H), 7.46 (tt, J=7.2, 1.5 Hz, 2H), 7.37 (tt, J=7.4, 1.4 Hz, 1H), 6.82 (d, J=2.6 Hz, 1H).
¹³C NMR (CDCl₃, 100 MHz) δ (ppm): 153.6, 140.5, 132.7, 132.2 (q, J=32.0 Hz), 130.1, 128.7, 128.4, 128.0, 125.9, 123.8 (q, J=273 Hz), 122.7 (q, J=3.9 Hz), 121.7, 121.7, 115.7 (q, J=3.9 Hz).
¹⁹F NMR (CDCl₃, 376 MHz) δ (ppm): −62.7.

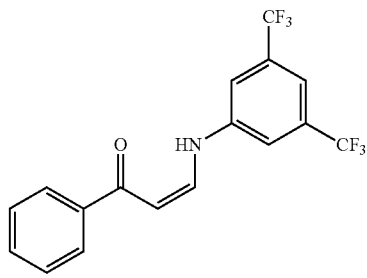
DJ030

¹H NMR (CDCl₃, 400 MHz) δ (ppm): 12.32 (d, J=11.8 Hz, 1H), 7.95 (dt, J=7.1, 1.4 Hz, 2H), 7.56-7.46 (m, 7H), 6.18 (d, J=8.3 Hz, 1H).
¹³C NMR (CDCl₃, 100 MHz) δ (ppm): 191.9, 142.9, 141.9, 138.5, 133.2 (q, J=33 Hz), 132.3, 128.6, 127.6, 123.0 (q, J=273 Hz), 116.3 (q, J=3 Hz), 115.7 (q, J=3 Hz), 96.2.
¹⁹F NMR (CDCl₃, 376 MHz) δ (ppm): −63.2.

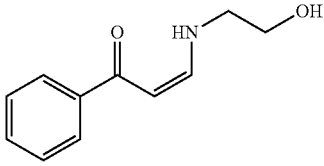
DJ031

¹H NMR (CDCl₃, 400 MHz) δ (ppm): 10.35 (br s, 1H), 7.86 (dt, J=6.7, 1.7 Hz, 2H), 7.47-7.38 (m, 3H), 6.98 (dd, J=12.6, 7.4 Hz, 1H), 5.71 (d, J=7.6 Hz, 1H), 3.76 (t, J=5.2 Hz, 2H), 3.40 (q, J=5.8 Hz, 2H), 2.51 (br s, 1H).
¹³C NMR (CDCl₃, 100 MHz) δ (ppm): 190.3, 154.9, 139.7, 131.0, 128.3, 127.1, 90.7, 62.4, 51.4.

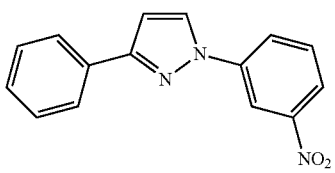
DJ032

¹H NMR (CDCl₃, 400 MHz) δ (ppm): 8.64 (t, J=2.1 Hz, 1H), 8.18-8.11 (m, 2H), 8.05 (d, J=2.6 Hz, 1H), 7.93 (dt, J=7.0, 1.5 Hz, 2H), 7.65 (t, J=8.2 Hz, 1H), 7.48-7.44 (m, 2H), 7.38 (tt, J=7.4, 2.1 Hz, 1H), 6.86 (d, J=2.6 Hz, 1H).
¹³C NMR (CDCl₃, 100 MHz) δ (ppm): 154.0, 149.0, 140.9, 132.4, 130.4, 128.8, 128.6, 128.0, 125.9, 124.1, 120.6, 113.5, 106.3.

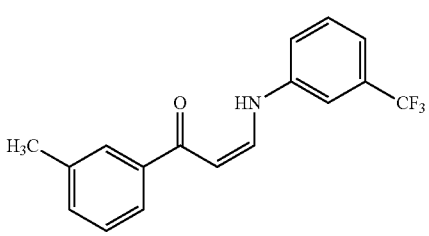
DJ033

¹H NMR (CDCl₃, 400 MHz) δ (ppm): 12.2 (d, J=11.6 Hz, 1H), 7.76 (s, 1H), 7.73 (dt, J=6.4, 2.3 Hz, 1H), 7.49 (dd, J=11.6, 7.9 Hz, 1H), 7.46 (t, J=8.0 Hz, 1H), 7.37-7.30 (m, 4H), 7.26-7.23 (m, 1H), 6.09 (d, J=7.9 Hz, 1H), 2.42 (s, 3H).
¹³C NMR (CDCl₃, 100 MHz) δ (ppm): 191.8, 143.8, 140.9, 138.9, 138.3, 132.7, 132.3 (q, J=33 Hz), 130.4, 128.4, 128.1, 124.6, 123.7 (q, J=273 Hz), 119.9 (q, J=4 Hz), 119.4, 112.6 (q, J=4 Hz), 95.1, 21.5.
¹⁹F NMR (CDCl₃, 376 MHz) δ (ppm): −62.3.

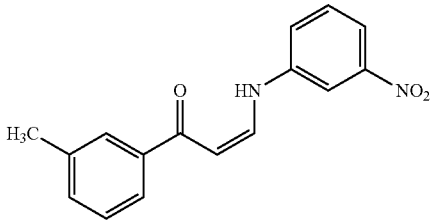
DJ034

¹H NMR (CDCl₃, 400 MHz) δ (ppm): 12.2 (d, J=11.9 Hz, 1H), 7.97 (t, J=2.3 Hz, 1H), 7.89 (ddd, J=8.1, 1.9, 0.9 Hz, 1H), 7.76 (s, 1H), 7.75-7.73 (m, 1H), 7.55-7.47 (m, 2H), 7.38-7.33 (m, 3H), 6.14 (d, J=8.1 Hz, 1H), 2.44 (s, 3H).
¹³C NMR (CDCl₃, 100 MHz) δ (ppm): 192.1, 149.5, 143.2, 141.7, 138.7, 138.4, 132.9, 130.6, 128.5, 128.1, 124.7, 122.3, 117.7, 109.9, 95.9, 21.5.

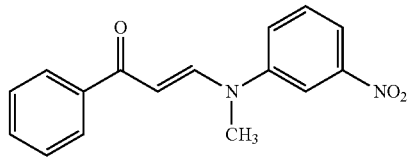
DJ035

¹H NMR (CDCl₃, 400 MHz) δ (ppm): 8.22 (d, J=12.8 Hz, 1H), 8.05-8.03 (m, 1H), 8.02-7.97 (m, 1H), 7.97-7.93 (m, 2H), 7.58-7.54 (m, 2H), 7.53 (tt, J=7.2, 2.5 Hz, 1H), 7.46 (tt, J=7.2, 1.5 Hz, 2H), 6.26 (d, J=12.8 Hz, 1H), 3.46 (s, 3H).
¹³C NMR (CDCl₃, 100 MHz) δ (ppm): 189.4, 149.1, 148.0, 147.3, 139.4, 131.9, 130.5, 128.4, 127.8, 125.3, 118.9, 114.3, 99.2, 36.9.

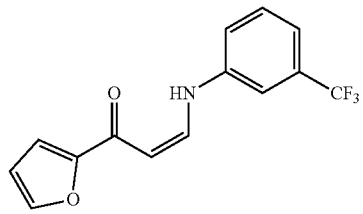
DJ036

¹H NMR (CDCl₃, 400 MHz) δ (ppm): 11.95 (d, J=11.4 Hz, 1H), 7.56 (dd, J=1.7, 0.8 Hz, 1H), 7.46 (dd, J=12.0, 8.0 Hz, 1H), 7.46-7.42 (m, 1H), 7.31-7.29 (m, 2H), 7.21 (dd, J=8.3, 1.9 Hz, 1H), 7.13 (dd, J=3.5, 0.7 Hz, 1H), 6.53 (dd, J=3.5, 1.7 Hz, 1H), 5.99 (d, J=7.9 Hz, 1H).
¹³C NMR (CDCl₃, 100 MHz) δ (ppm): 180.4, 153.5, 145.4, 143.9, 140.8, 132.3 (q, J=33 Hz), 130.4, 123.8 (q, J=277 Hz), 119.9 (q, J=4 Hz), 119.4, 114.8, 112.5 (q, J=4 Hz), 112.3, 94.7.
¹⁹F NMR (CDCl₃, 376 MHz) δ (ppm): −62.9.

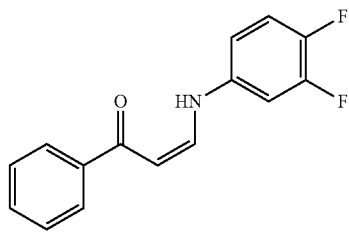
DJ037

¹H NMR (CDCl₃, 400 MHz) δ (ppm): 12.11 (d, J=11.8 Hz, 1H), 7.95-7.90 (m, 2H), 7.54-7.43 (m, 3H), 7.36 (dd, J=11.8, 7.8 Hz, 1H), 7.17-7.10 (m, 1H), 6.96-6.89 (m, 1H), 6.82-6.77 (m, 1H), 6.05 (d, J=7.9 Hz, 1H).
¹³C NMR (CDCl₃, 100 MHz) δ (ppm): 191.4, 150.9 (d, J=249, 14 Hz), 146.8 (d, J=244, 12 Hz), 144.6, 138.8, 137.2 (d, J=4 Hz), 131.9, 128.5, 127.4, 118.2 (dd, J=18, 2 Hz), 112.2 (dd, J=5, 3 Hz), 105.4 (d, J=21 Hz), 94.5.

¹⁹F NMR (CDCl₃, 376 MHz) δ (ppm): −134.7 (d), −144.0 (d).

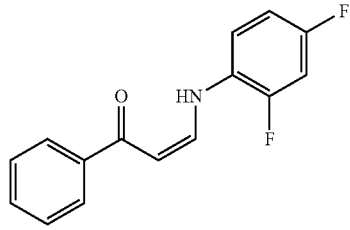
DJ038

¹H NMR (CDCl₃, 400 MHz) δ (ppm): 12.13 (d, J=11.4 Hz, 1H), 7.98-7.92 (m, 2H), 7.54-7.38 (m, 4H), 7.19-7.13 (m, 1H), 6.96-6.85 (m, 2H), 6.10 (d, J=7.8 Hz, 1H).

¹³C NMR (CDCl₃, 100 MHz) δ (ppm): 191.3, 158.3 (dd, J=245, 11 Hz), 152.4 (dd, J=248, 11 Hz), 144.4, 138.9, 131.8, 128.5, 127.4, 125.6 (dd, J=11, 4 Hz), 116.4 (dd, J=9, 3 Hz), 111.7 (dd, J=23, 4 Hz), 104.9 (dd, J=26, 23 Hz), 94.9.

¹⁹F NMR (CDCl₃, 376 MHz) δ (ppm): −116.5 (d), −125.6 (d).

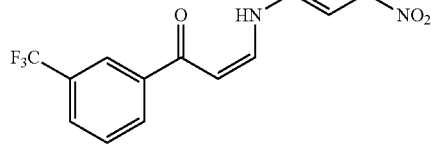
DJ039

¹H NMR (CDCl₃, 400 MHz) δ (ppm): 12.28 (d, J=11.8 Hz, 1H), 8.19 (s, 1H), 8.12 (d, J=8.0 Hz, 1H), 8.00 (t, J=2.3 Hz, 1H), 7.94 (ddd, J=8.0, 2.0, 0.8 Hz, 1H), 7.78 (d, J=7.9 Hz, 1H), 7.63-7.51 (m, 3H), 7.40 (ddd, J=8.0, 2.0, 0.8 Hz, 1H), 6.14 (d, J=7.8 Hz, 1H).

¹³C NMR (CDCl₃, 100 MHz) δ (ppm): 189.9, 149.4, 144.4, 141.3, 129.3, 131.1 (q, J=33 Hz), 130.7, 130.6, 129.2, 128.5 (q, J=4 Hz), 124.4 (q, J=4 Hz), 123.8 (q, J=273 Hz), 122.4, 118.2, 110.3, 95.1.

¹⁹F NMR (CDCl₃, 376 MHz) δ (ppm): −62.7.

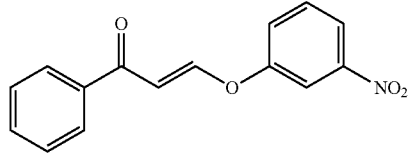
DJ040

¹H NMR (CDCl₃, 400 MHz) δ (ppm): 8.09 (ddd, J=8.3, 2.3, 0.9 Hz, 1H), 8.01 (t, J=2.3 Hz, 1H), 7.97 (d, J=11.8 Hz, 1H), 7.95-7.93 (m, 2H), 7.62-7.56 (m, 2H), 7.52-7.46 (m, 3H), 6.86 (d, J=11.8 Hz, 1H).

¹³C NMR (CDCl₃, 100 MHz) δ (ppm): 189.9, 157.8, 156.4, 149.3, 137.9, 133.1, 130.9, 128.7, 128.2, 123.8, 119.8, 113.1, 108.5.

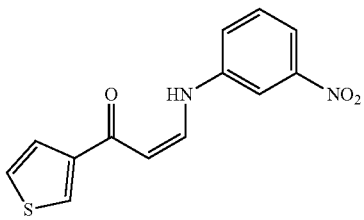
DJ043

¹H NMR (CDCl₃, 400 MHz) δ (ppm): 12.08 (d, J=11.5 Hz, 1H), 8.00 (dd, J=2.9, 1.2 Hz, 1H), 7.94 (t, J=2.1 Hz, 1H), 7.88 (ddd, J=8.2, 2.0, 0.8 Hz, 1H), 7.55 (dd, J=5.1, 1.1 Hz, 1H), 7.51-7.44 (m, 2H), 7.36-7.31 (m, 2H), 5.97 (d, J=8.0 Hz, 1H).

¹³C NMR (CDCl₃, 100 MHz) δ (ppm): 186.2, 149.4, 143.3, 143.0, 141.6, 130.6, 130.0, 126.7, 126.4, 122.1, 117.7, 109.9, 96.8.

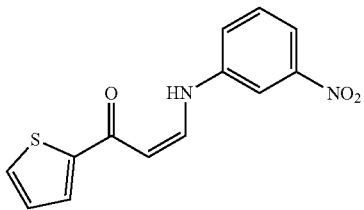
DJ044

¹H NMR (CDCl₃, 400 MHz) δ (ppm): 11.96 (d, J=12.1 Hz, 1H), 7.92 (t, J=2.2 Hz, 1H), 7.88 (ddd, J=8.1, 2.2, 0.8 Hz, 1H), 7.68 (dd, J=3.8, 1.1 Hz, 1H), 7.59 (dd, J=4.9, 1.1 Hz, 1H), 7.50-7.44 (m, 2H), 7.32 (ddd, J=8.1, 2.3, 0.8 Hz, 1H), 7.13 (dd, J=4.9, 3.8 Hz, 1H), 5.99 (d, J=7.9 Hz, 1H).

¹³C NMR (CDCl₃, 100 MHz) δ (ppm): 184.4, 149.4, 145.6, 142.9, 141.6, 132.5, 130.6, 129.8, 128.2, 122.2, 117.7, 109.8, 95.8.

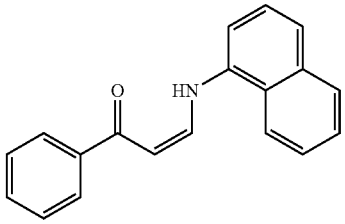
DJ045

¹H NMR (CDCl₃, 400 MHz) δ (ppm): 13.08 (d, J=11.2 Hz, 1H), 8.26 (d, J=8.6 Hz, 1H), 8.02-7.99 (m, 2H), 7.87 (dt, J=8.2, 0.7 Hz, 1H), 7.72 (dd, J=11.6, 7.8 Hz, 1H), 7.64-7.60 (m, 2H), 7.52-7.43 (m, 5H), 7.29 (d, J=7.9 Hz, 1H), 6.17 (d, J=7.9 Hz, 1H).

¹³C NMR (CDCl₃, 100 MHz) δ (ppm): 191.4, 146.2, 139.3, 136.5, 134.4, 131.7, 128.5, 127.4, 126.7, 126.6, 125.8, 124.9, 124.2, 121.1, 111.1, 94.7.

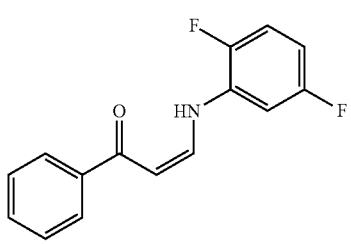
DJ046

¹H NMR (CDCl₃, 400 MHz) δ (ppm): 12.14 (d, J=11.5 Hz, 1H), 7.97-7.94 (m, 2H), 7.52 (tt, J=7.6, 2.4 Hz, 1H), 7.48-7.44 (m, 2H), 7.39 (dd, J=11.5, 7.9 Hz, 1H), 7.12-7.06 (m, 1H), 6.94-6.90 (m, 1H), 6.71-6.64 (m, 1H), 6.15 (d, J=7.9 Hz, 1H).

¹³C NMR (CDCl₃, 100 MHz) δ (ppm): 191.6, 159.2 (dd, J=243, 3 Hz), 148.4 (dd, J=241, 3 Hz), 142.9, 138.8, 132.0, 130.0 (dd, J=13, 10 Hz), 128.5, 127.5, 116.8 (dd, J=21, 10 Hz), 109.1 (dd, J=24, 8 Hz), 102.3 (dd, J=28, 3 Hz), 95.9.

¹⁹F NMR (CDCl₃, 376 MHz) δ (ppm): −136.3 (d), −116.3 (d).

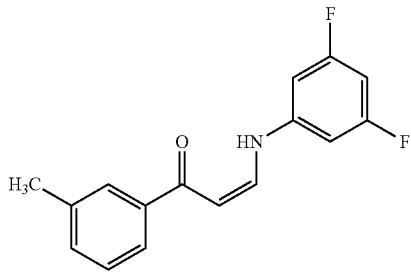
DJ047

¹H NMR (CDCl₃, 400 MHz) δ (ppm): 12.06 (d, J=11.8 Hz, 1H), 7.75 (s, 1H), 7.73-7.70 (m, 1H), 7.36 (dd, J=11.7, 8.2 Hz, 1H), 7.36-7.33 (m, 2H), 6.64-6.56 (m, 2H), 6.49 (tt, J=8.9, 2.1 Hz, 1H), 6.08 (d, J=8.2 Hz, 1H), 2.43 (s, 3H).

¹³C NMR (CDCl₃, 100 MHz) δ (ppm): 191.9, 164.0 (dd, J=247, 14 Hz), 143.3, 142.9 (d, J=13 Hz), 138.7, 138.3, 132.9, 128.4, 128.1, 124.6, 99.2 (dd, J=20, 9 Hz), 98.5 (t, J=26 Hz), 95.5, 21.4.

¹⁹F NMR (CDCl₃, 376 MHz) δ (ppm): −107.9.

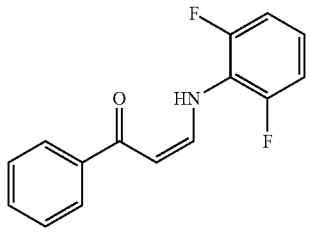
DJ048

¹H NMR (CDCl₃, 400 MHz) δ (ppm): 12.16 (d, J=10.9 Hz, 1H), 7.97-7.94 (m, 2H), 7.72 (dd, J=12, 8 Hz, 1H), 7.51 (tt, J=7.3, 2.7 Hz, 1H), 7.48-7.43 (m, 2H), 6.99-6.93 (m, 3H), 6.10 (d, J=8.2 Hz, 1H).

¹³C NMR (CDCl₃, 100 MHz) δ (ppm): 191.6, 153.5 (dd, J=247, 7 Hz), 147.6 (t, J=6 Hz), 138.9, 131.8, 128.5, 127.5, 122.6 (t, J=9 Hz), 112.2 (dd, J=17, 7 Hz), 95.3.

¹⁹F NMR (CDCl₃, 376 MHz) δ (ppm): −125.5.

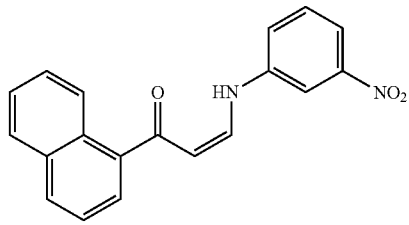
DJ049

¹H NMR (CDCl₃, 400 MHz) δ (ppm): 12.26 (d, J=11.8 Hz, 1H), 8.52 (dd, J=8.3, 0.8 Hz, 1H), 8.01 (t, J=2.1 Hz, 1H), 7.95 (d, J=8.3 Hz, 1H), 7.92 (ddd, J=8.3, 2.1, 1.1 Hz, 1H), 7.89 (dd, J=8.2, 1.4 Hz, 1H), 7.76 (dd, J=7.2, 1.2 Hz, 1H), 7.60-7.49 (m, 5H), 7.41 (ddd, J=8.2, 2.3, 0.9 Hz, 1H), 5.98 (d, J=8.0 Hz, 1H).

¹³C NMR (CDCl₃, 100 MHz) δ (ppm): 196.1, 149.5, 143.1, 141.7, 138.2, 133.9, 131.3, 130.7, 130.1, 128.5, 127.2, 126.4, 126.3, 125.7, 124.7, 122.4, 117.9, 110.1, 100.2.

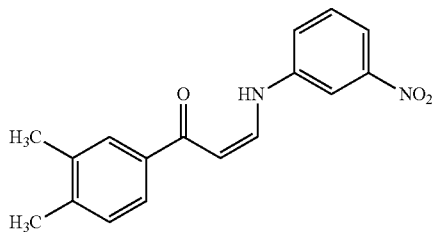
DJ050

¹H NMR (CDCl₃, 400 MHz) δ (ppm): 12.2 (d, J=11.6 Hz, 1H), 7.95 (t, J=2.1 Hz, 1H), 8.87 (ddd, J=8.2, 2.2, 0.9 Hz, 1H), 7.73 (s, 1H), 7.67 (dd, J=7.9, 1.7 Hz, 1H), 7.50 (dd, J=11.6, 8.2 Hz, 1H), 7.47 (d, J=8.1 Hz, 1H), 7.35 (ddd, J=8.1, 2.3, 0.9 Hz, 1H), 7.22 (d, J=7.8 Hz, 1H), 6.13 (d, J=8.2 Hz, 1H), 2.33 (s, 3H), 2.32 (s, 3H).

¹³C NMR (CDCl₃, 100 MHz) δ (ppm): 191.8, 149.4, 142.9, 141.8, 141.6, 136.9, 136.4, 130.6, 129.8, 128.7, 125.2, 122.2, 117.6, 109.8, 95.8, 20.0, 19.9.

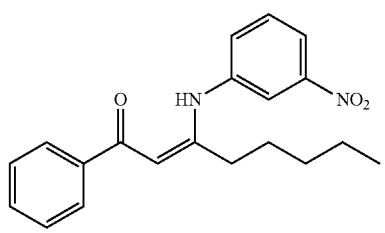
DJ052

¹H NMR (CDCl₃, 400 MHz) δ (ppm): 13.29 (s, 1H), 8.09-8.04 (m, 2H), 7.95-7.90 (m, 2H), 7.52-7.48 (m, 5H), 6.02 (s, 1H), 2.49 (t, J=7.6 Hz, 2H), 1.63-1.55 (m, 2H), 1.36-1.22 (m, 4H), 0.85 (t, J=7.0 Hz, 3H).

¹³C NMR (CDCl₃, 100 MHz) δ (ppm): 189.9, 165.2, 148.8, 140.2, 139.6, 131.4, 130.3, 130.1, 128.4, 127.2, 120.1, 119.0, 94.8, 32.4, 31.4, 28.0, 22.2, 13.8.

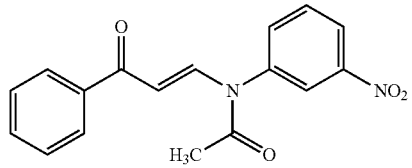
DJ053

¹H NMR (CDCl₃, 400 MHz) δ (ppm): 8.67 (d, J=13.6 Hz, 1H), 8.41 (ddd, J=8.4, 2.2, 0.9 Hz, 1H), 8.17 (t, J=2.2 Hz, 1H), 7.80 (t, J=8.2 Hz, 1H), 7.72-7.69 (m, 2H), 7.62 (ddd, J=7.8, 2.0, 0.8 Hz, 1H), 7.51 (tt, J=7.4, 1.4 Hz, 1H), 7.42-7.37 (m, 2H), 5.74 (d, J=13.6 Hz, 1H), 2.20 (brs, 3H).

¹³C NMR (CDCl₃, 100 MHz) δ (ppm): 189.8, 169.2, 149.5, 142.8, 139.5, 138.1, 134.7, 132.7, 131.5, 128.5, 128.1, 124.5, 123.9, 107.3, 23.2.

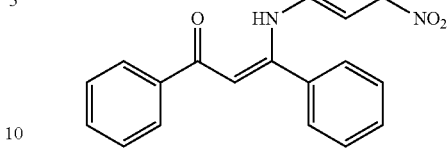
DJ057

¹H NMR (CDCl₃, 400 MHz) δ (ppm): 12.91 (s, 1H), 8.00-7.96 (m, 2H), 7.81 (ddd, J=8.1, 2.1, 1.0 Hz, 1H), 7.58 (t, J=2.1 Hz, 1H), 7.53 (tt, J=7.3, 1.3 Hz, 1H), 7.49-7.37 (m, 7H), 7.28 (t, J=8.4 Hz, 1H), 7.07 (dd, J=8.1, 2.1 Hz, 1H), 6.22 (s, 1H).

¹³C NMR (CDCl₃, 100 MHz) δ (ppm): 190.6, 160.2, 148.5, 141.1, 139.3, 134.9, 131.9, 130.4, 129.5, 129.1, 128.5, 128.2, 128.1, 127.5, 118.3, 117.1, 98.9.

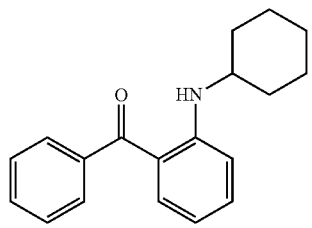
DJ055

¹H NMR (CDCl₃, 400 MHz) δ (ppm): 8.75 (d, J=6.6 Hz, 1H), 7.62-7.57 (m, 2H), 7.52-7.41 (m, 4H), 7.34 (tdd, J=7.3, 1.7, 1.4 Hz, 1H), 6.79 (d, J=8.7 Hz, 1H), 6.46 (tdd, J=7.0, 1.2, 1.0 Hz, 1H), 3.54-3.44 (m, 1H), 2.11-2.00 (m, 2H), 1.88-1.73 (m, 2H), 1.67-1.58 (m, 1H), 1.49-1.26 (m, 5H).

¹³C NMR (CDCl₃, 100 MHz) δ (ppm): 199.3, 151.1, 140.8, 135.8, 134.9, 130.6, 129.0, 128.0, 116.8, 113.1, 112.0, 50.5, 32.7, 25.9, 24.6.

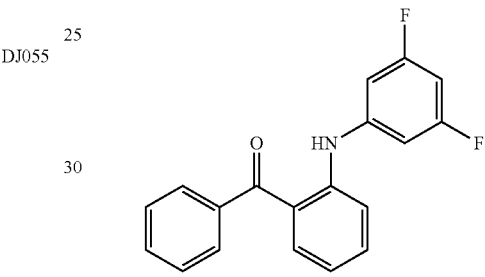
DJ058

¹H NMR (CDCl₃, 400 MHz) δ (ppm): 9.95 (s, 1H), 7.74-7.71 (m, 2H), 7.60-7.55 (m, 2H), 7.52-7.46 (m, 3H), 7.46-7.41 (m, 1H), 6.88-6.83 (m, 1H), 6.80-6.74 (m, 2H), 6.45 (tt, J=8.8, 2.1 Hz, 1H).

¹³C NMR (CDCl₃, 100 MHz) δ (ppm): 199.1, 163.9 (dd, J=246, 15 Hz), 145.4, 143.8 (t, J=13 Hz), 139.1, 134.7, 134.1, 132.0, 129.7, 128.3, 122.0, 118.7, 116.4, 102.7 (dd, J=20, 8 Hz), 97.7 (dd, J=27, 26 Hz).

¹⁹F NMR (CDCl₃, 376 MHz) δ (ppm): −109.3.

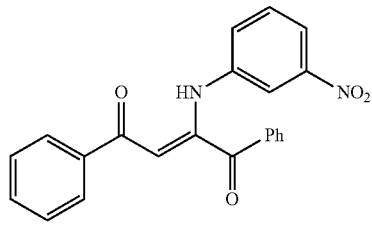
DJ056

¹H NMR (CDCl₃, 400 MHz) δ (ppm): 12.61 (s, 1H), 8.03-7.98 (m, 2H), 7.97-7.92 (m, 2H), 7.85-7.81 (m, 2H), 7.60 (tt, J=7.5, 1.3 Hz, 1H), 7.55 (tt, J=7.3, 1.4 Hz, 1H), 7.50-7.43 (m, 4H), 7.33 (t, J=7.1 Hz, 1H), 7.25 (dt, J=8.5, 1.8 Hz, 1H), 6.26 (s, 1H).

¹³C NMR (CDCl₃, 100 MHz) δ (ppm): 191.7, 191.6, 155.1, 148.7, 140.2, 138.5, 134.9, 134.5, 132.6, 130.1, 129.8, 129.1, 128.7, 127.6, 126.7, 119.2, 115.9, 97.5.

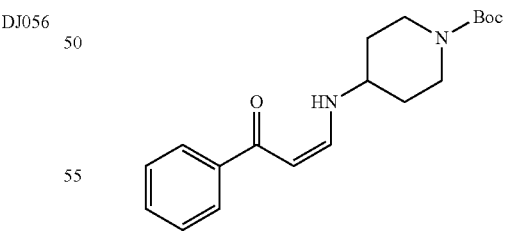
DJ059

¹H NMR (CDCl₃, 400 MHz) δ (ppm): 10.43 (dd, J=12.0, 7.9 Hz, 1H), 7.87-7.84 (m, 2H), 7.46-7.37 (m, 3H), 7.00 (dd, J=12.8, 7.6 Hz, 1H), 5.72 (d, J=7.6 Hz, 1H), 4.07-3.96 (m, 2H), 3.32-3.22 (m, 1H), 2.92 (t, J=11.9 Hz, 2H), 1.97-1.86 (m, 2H), 1.62-1.48 (m, 2H), 1.45 (s, 9H).

¹³C NMR (CDCl₃, 100 MHz) δ (ppm): 190.1, 154.7, 151.9, 139.6, 131.0, 128.3, 127.1, 90.6, 79.9, 55.5, 42.1, 33.0, 28.4.

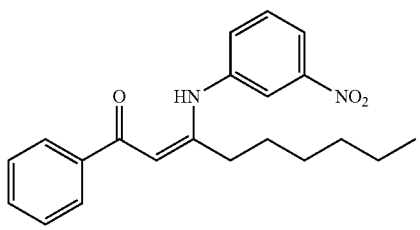

DJ060

¹H NMR (CDCl₃, 400 MHz) δ (ppm): 13.3 (s, 1H), 8.07-8.04 (m, 2H), 7.95-7.89 (m, 2H), 7.58-7.42 (m, 5H), 6.02 (s, 1H), 2.49 (t, J=8.3 Hz, 1H), 1.63-1.53 (m, 2H), 1.38-1.17 (m, 6H), 0.85 (t, J=6.7 Hz, 3H).

¹³C NMR (CDCl₃, 100 MHz) δ (ppm): 189.9, 165.2, 148.8, 140.2, 139.6, 131.4, 130.3, 130.1, 128.4, 127.2, 120.0, 119.0, 94.8, 32.5, 31.4, 28.9, 28.3, 22.4, 14.0.

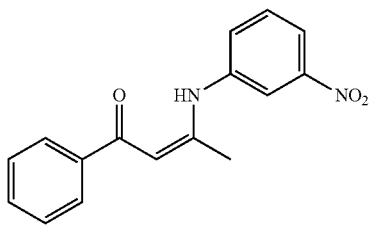

DJ061

¹H NMR (CDCl₃, 400 MHz) δ (ppm): 13.3 (s, 1H), 8.06-8.01 (m, 2H), 7.94-7.89 (m, 2H), 7.56-7.41 (m, 5H), 5.99 (s, 1H), 2.24 (s, 3H).

¹³C NMR (CDCl₃, 100 MHz) δ (ppm): 189.7, 160.4, 148.8, 140.3, 139.4, 131.5, 130.1, 129.7, 128.4, 127.2, 119.8, 118.5, 96.1, 20.6.

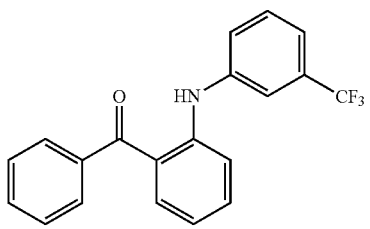

DJ062

¹H NMR (CDCl₃, 400 MHz) δ (ppm): 10.09 (s, 1H), 7.74-7.70 (m, 2H), 7.59-7.53 (m, 3H), 7.51-7.46 (m, 2H), 7.46-7.39 (m, 4H), 7.31-7.27 (m, 1H), 6.83-6.78 (m, 1H).

¹³C NMR (CDCl₃, 100 MHz) δ (ppm): 199.2, 146.6, 141.6, 139.4, 134.9, 134.3, 131.9 (q, J=32 Hz), 131.8, 130.0, 129.6, 128.2, 124.2, 124.0 (q, J=273 Hz), 121.0, 119.4 (q, J=4 Hz), 117.9, 117.6 (q, J=4 Hz), 115.1.

Example 2: Effect of DJ001 and DJ003 on Survival of Irradiated Mice

DJ001 activates Rac1 signaling in HSCs, accelerates HSC regeneration in irradiated mice and dramatically increases mice survival following lethal dose irradiation, as shown in FIG. 1. A) CFU-GEMMs produced by TSF media vs. TSF+GJ001 (p=0.001). B) Percentage of BM KSL cells expressing Rac1 GTP (p=0.008). C) Survival of mice irradiated with 750 cGy followed by treatment with DJ001 or vehicle (p=0.0007). D) % BM KSL cells (blue) and % ckit⁺sca-1⁻lin⁻ progenitors (gray) at day+21 in irradiated mice.

Figure 2A:
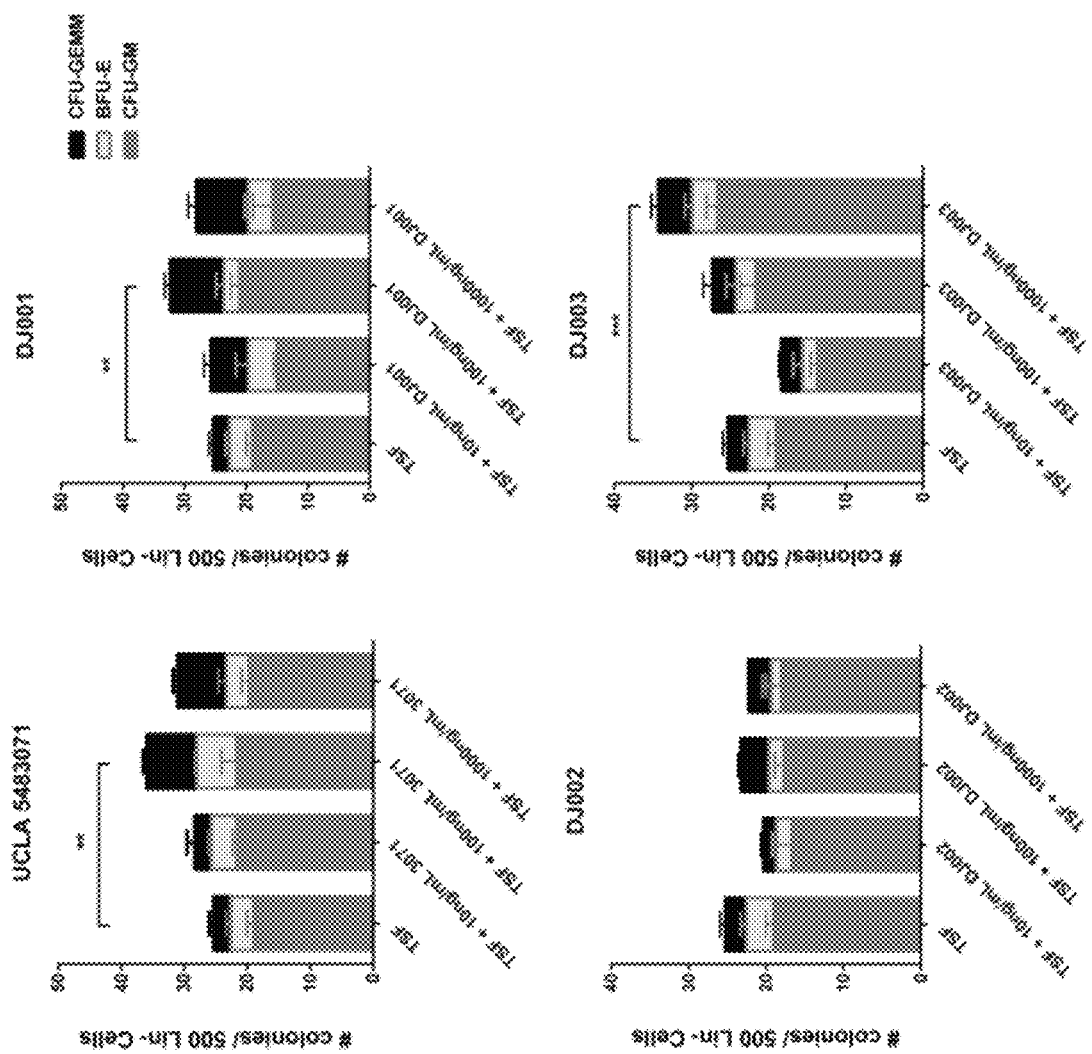
FIGS. 2A and 2B show that Novel PTPσ inhibitor, DJ003 increases hematopoietic colony formation (2A) and improves survival of irradiated mice (2B).
Figure 2B:
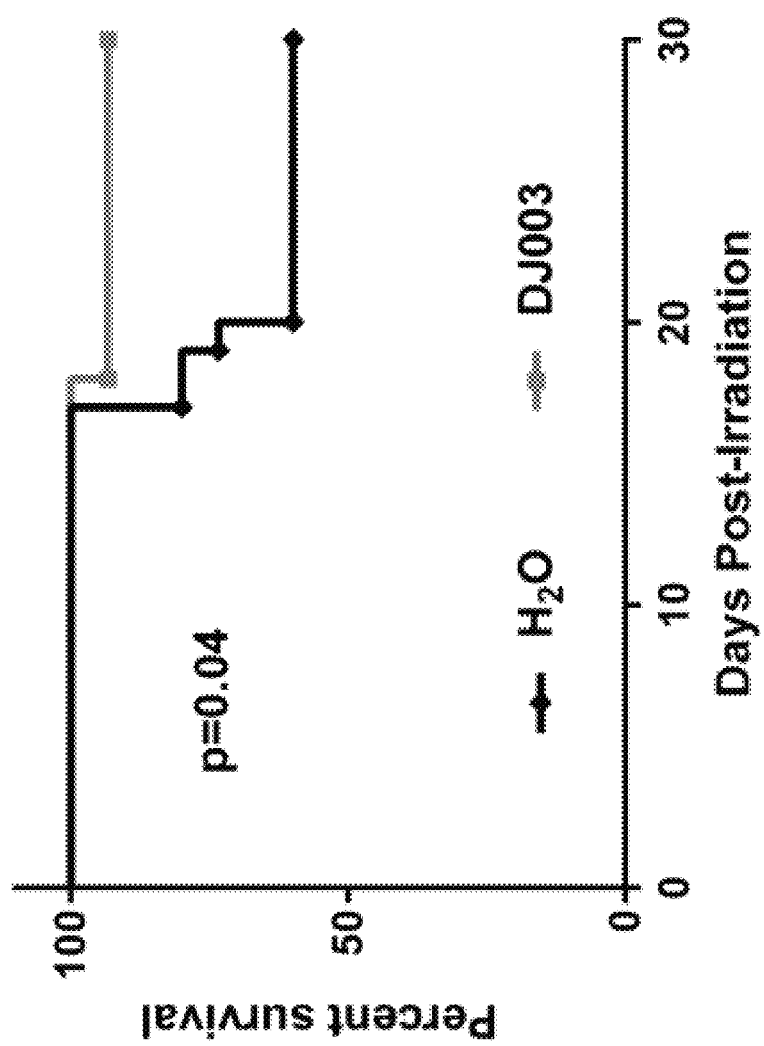

FIG. 2 shows that DJ003 increases hematopoietic colony formation (FIG. 2A) and improves survival of irradiated mice (FIG. 2B).

Example 2: Rac1 Activation Assay

Cell cultures were incubated with each tested compound for 2 minutes at concentrations of 1 and 10 μg/mL, after which the cells were tested for Rac1 activation using a G-LISA activation assay. The cells were lysed and the lysates introduced into wells containing Rac-GTP-binding protein, then sequentially incubated with anti-Rac1 antibody and a horseradish peroxidase-linked secondary antibody. The amount of horseradish peroxidase was then quantitated to evaluate the Rac1 activation potency of each compound studied. The results are shown in Table 2.

TABLE 2

| Compound | Rac1 Activation | Potency relative to EGF control = ++++ |
|---|---|---|
| DJ001 | yes | ++++ |
| DJ002 | no | |
| DJ003 | yes | ++ |
| DJ004 | yes | ++ |
| DJ005 | no | |
| DJ006 | no | |
| DJ007 | no | |
| DJ008 | no | |
| DJ009 | yes | ++++ |
| DJ011 | yes | ++++ |
| DJ012 | yes | ++++ |
| DJ013 | yes | ++++ |
| DJ014 | yes | ++++ |
| DJ015 | yes | ++++ |
| DJ016 | no | |
| DJ017 | no | |
| DJ018 | no | |
| DJ019 | no | |

Example 3: Rac1 Activation Assay

Figure 3:
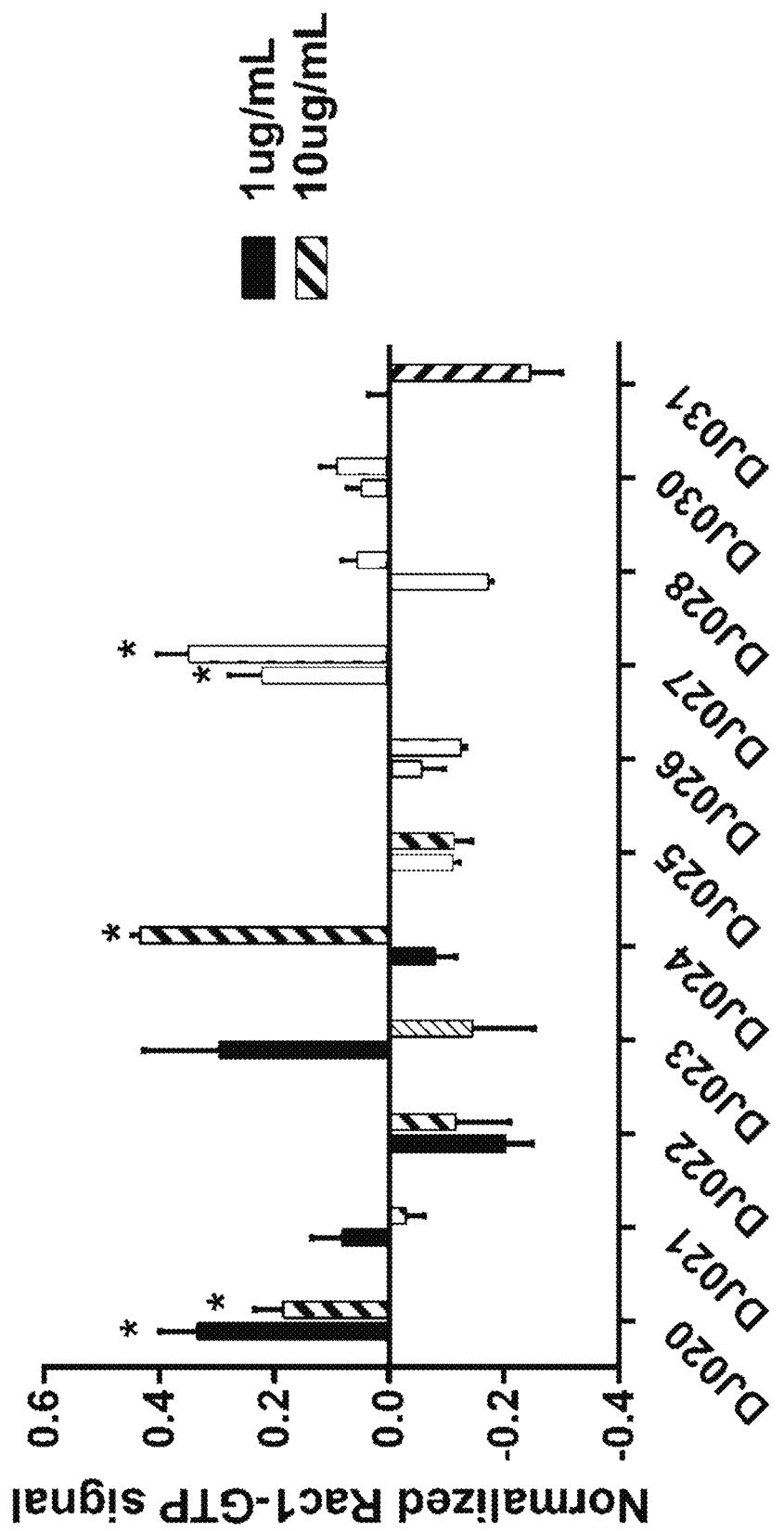
FIG. 3 shows the effect of various compounds on Rac1 activation in bone marrow cells.
Figure 5A:
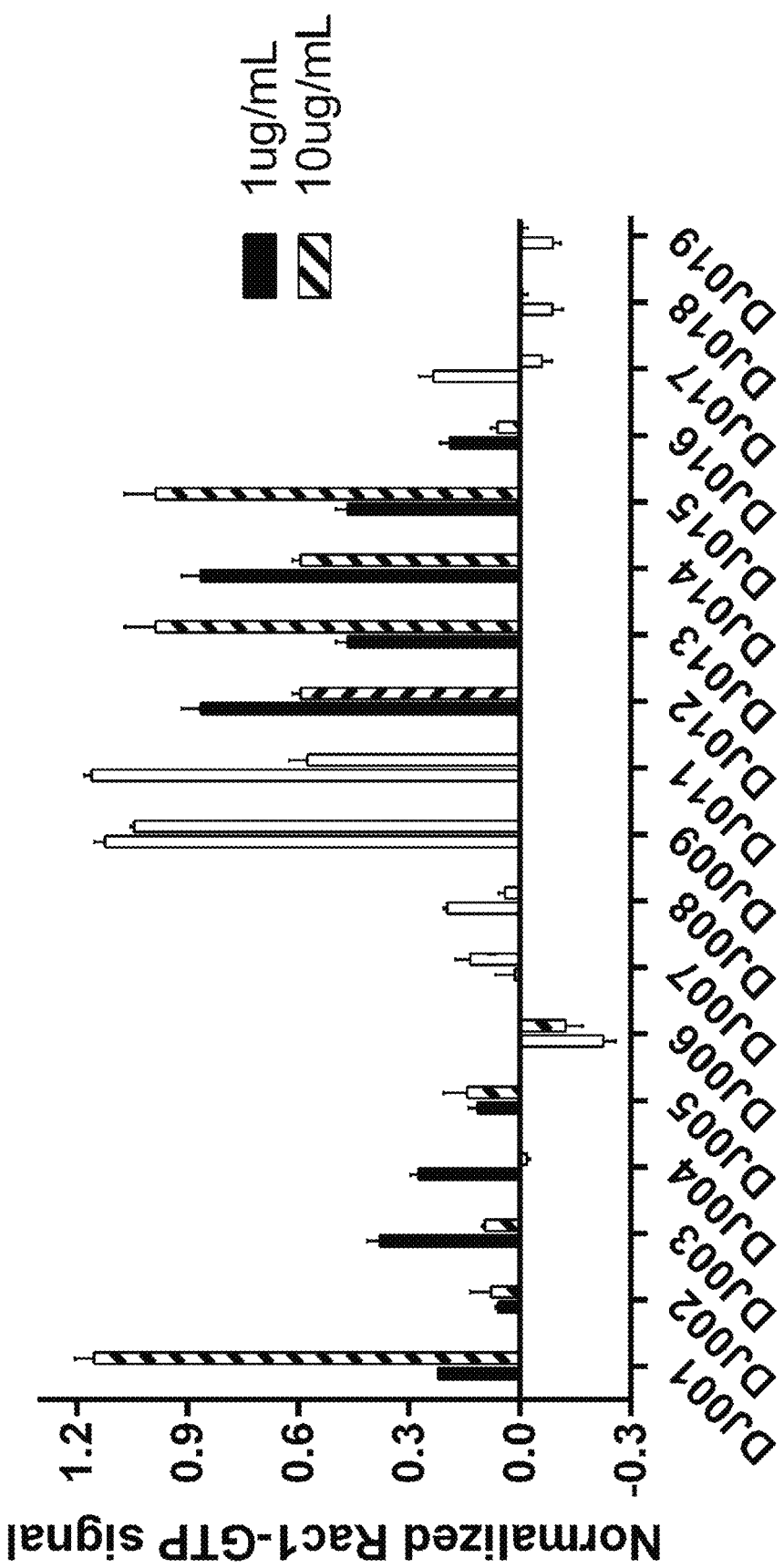
FIGS. 5A and 5B show the effect of various compounds on Rac1 activation in bone marrow cells.
Figure 5B:
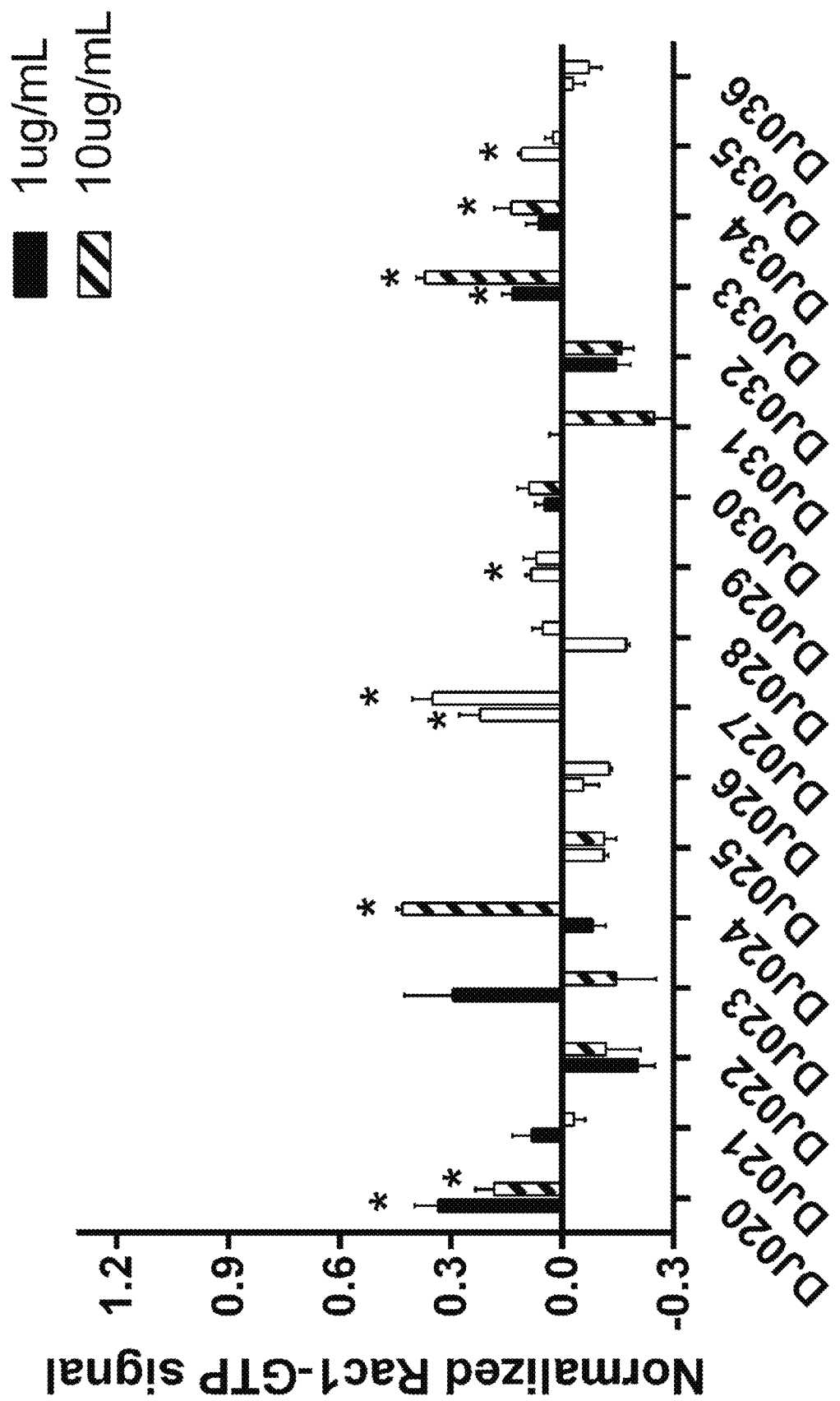

Compounds DJ001-DJ009 and DJ011-DJ036 were assayed as described in Example 3. The results are presented in FIGS. 3, 5A, and 5B.

Example 4: Mouse Survival Study

Figure 4:
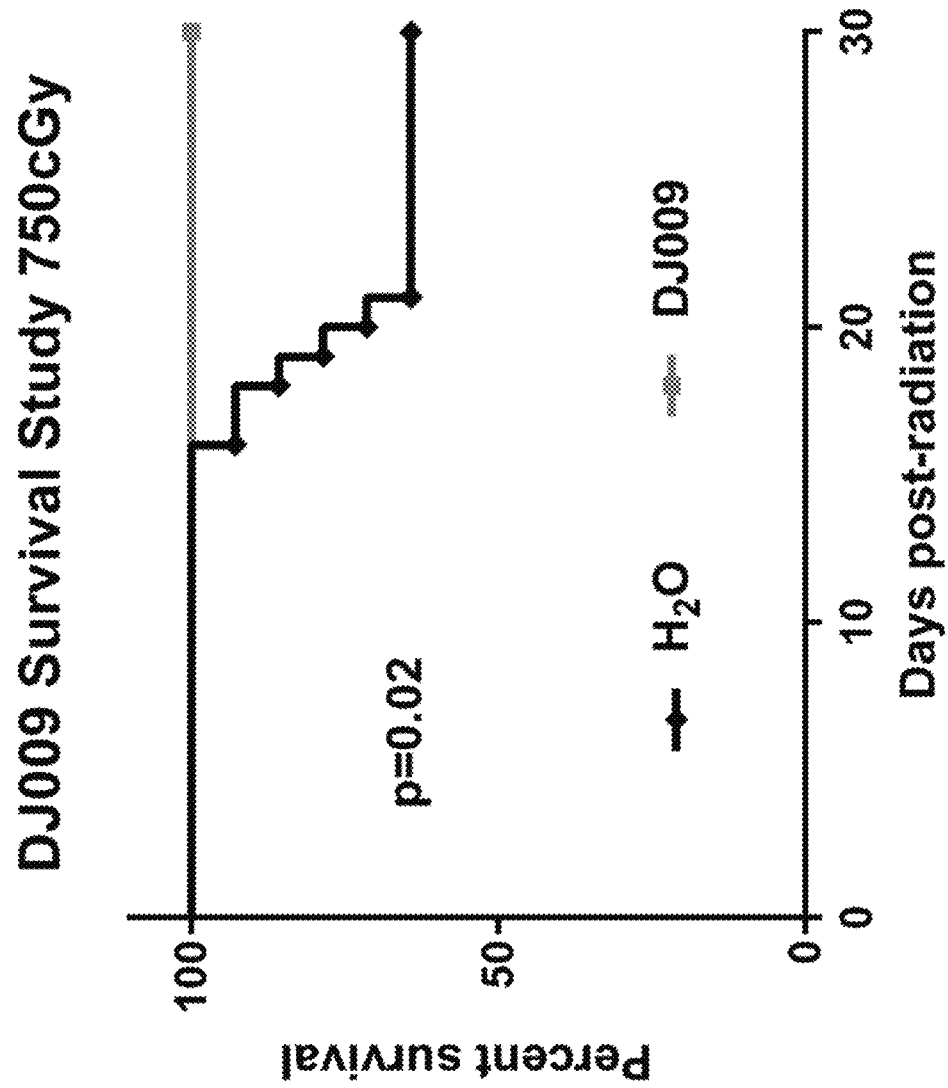
FIG. 4 shows the survival of mice subjected to 750 cGy of radiation, and treated with either DJ009 or a control (water).

Mice were subjected to 750 cGy of radiation and treated with either water or DJ009. The results are depicted in FIG. 4.

Example 45: In Vitro Phosphatase Assay

The two interacellular catalytic domains (D1D2) of PTPRS were cloned into a pET28a vector and overexpressed in *E. coli* BL21 and purified as described in Jeon T J, et al. Structure of the Catalytic Domain of Protein Tyrosine Phosphatase Sigma in the Sulfenic Acid Form. Molecules and Cells. 2013; 36(1):55-61. doi:10.1007/s10059-013-0033-x. Enzymatic activity of PTPRS was assayed using a modified version of the Malachite Green Assay (described in Lorenz U. Protein Tyrosine Phosphatase Assays. Current protocols in immunology/edited by John E Coligan. [et al]. 2011;

CHAPTER:Unit-11.7. doi:10.1002/0471142735.im1107s93) and the Tyrosine Phosphatase Assay Kit (Promega Coorperation). Unless stated otherwise, standard assays were carried out using 50 nM PTPRS protein in 1× Buffer (10 mM Tris, 5 mM MgCl2, 10 mM NaCl, 0.02% Tween) and Tyr Phosphopeptide as substrate (100 uM for FIG. 1 and 50-1200 uM in FIG. 2). Catalytic domains D1D2 were preincubated with the test compound or control for 15 min in the wells of a 96 well plate before the addition of 100 uM Tyr Phosphopeptide (DADA(pY)LIPQQG).

For $IC_{50}$ determination, rates normalized relative to uninhibited controls (DMSO) were plotted against compound concentration and fitted using a four-parameter nonlinear regression curve fit ((y=[(A-D) (1+{xC-1}B)-1]+D), (Prism 6.0, Graphpad Software). For mechanism studies and determination of the enyzme's $K_m$ and $V_{max}$, data were analyzed using a nonlinear regression fit according to classical Mechaelis-Menten kinetics model $Y=V_{max}*X/(K_m+X)$ (Prism 6.0, Graphpad Software).

Figure 6A:
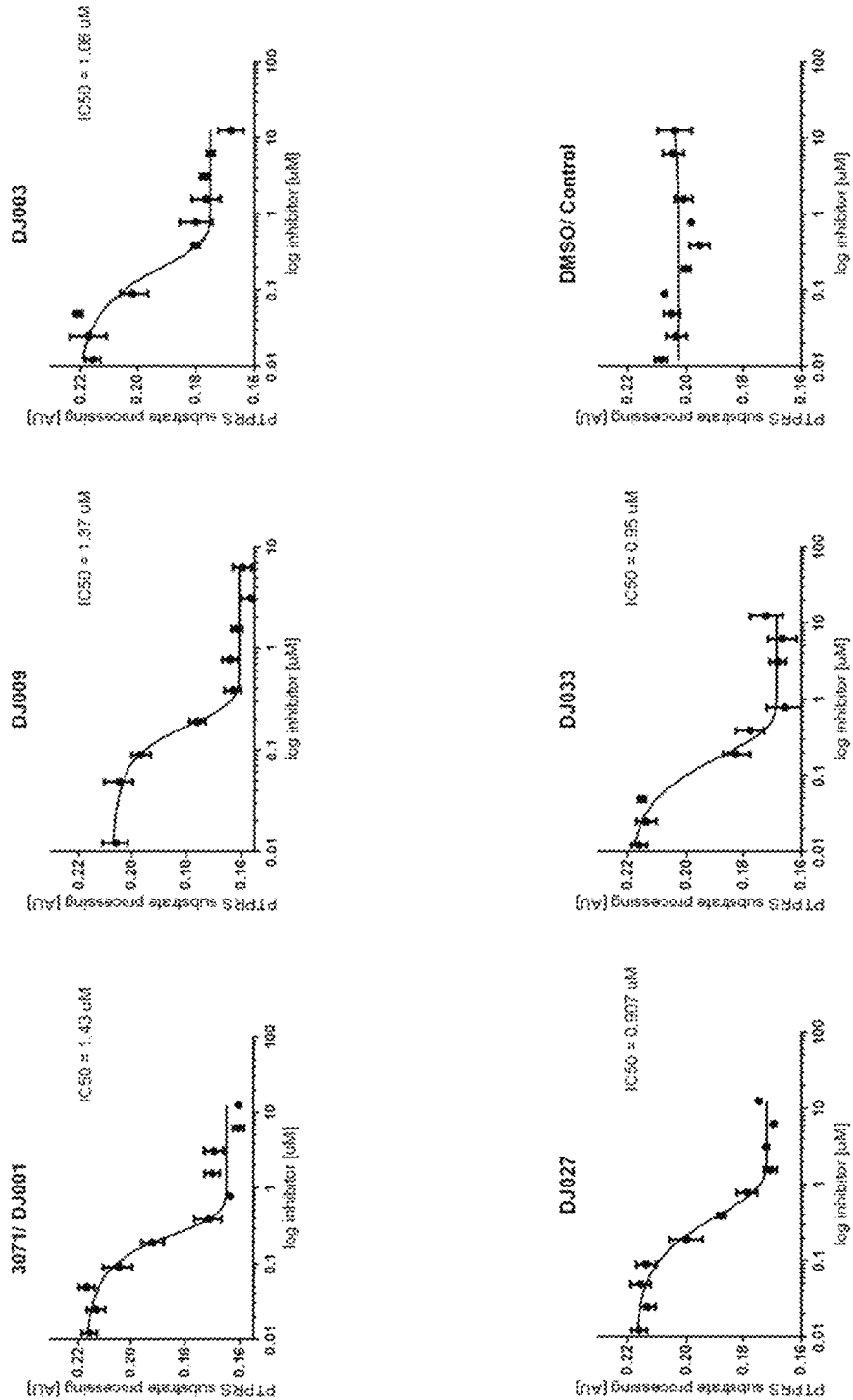
FIGS. 6A and 6B show the inhibition of PTPσ by various compounds.
Figure 6B:
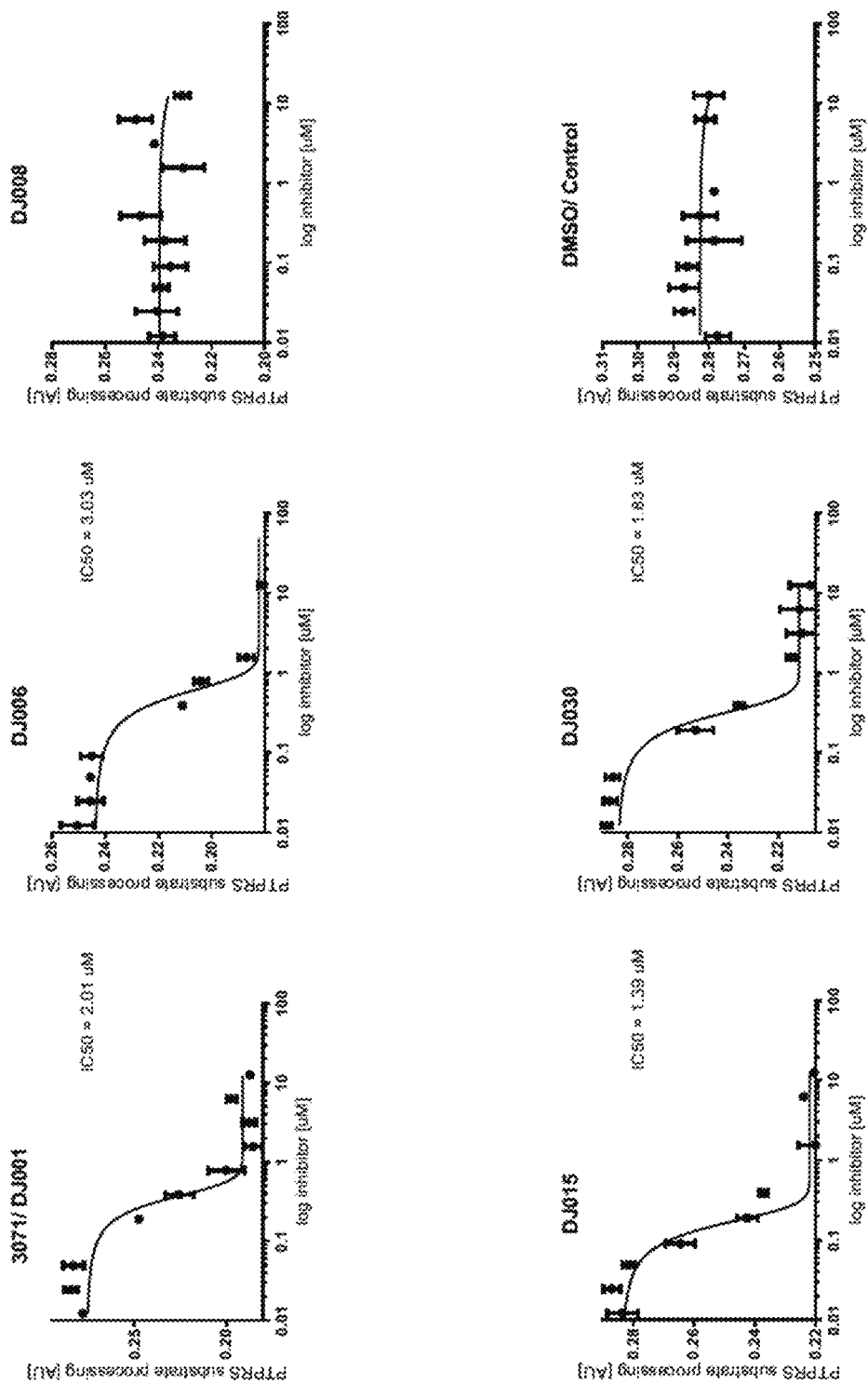

The IC50s measured are listed in Table 3. Activity data as a function of inhibitor concentration is shows in FIGS. 6A and 6B.

TABLE 3

| Compound | $IC_{50}$ (μM) |
|---|---|
| DJ001 | 1.43 |
| DJ003 | 1.06 |
| DJ006 | 3.03 |
| DJ008 | N/D |
| DJ009 | 1.37 |
| DJ015 | 1.39 |
| DJ027 | 0.91 |
| DJ030 | 1.83 |
| DJ033 | 0.95 |

Example 6: Mechanistic Study

Figure 7:
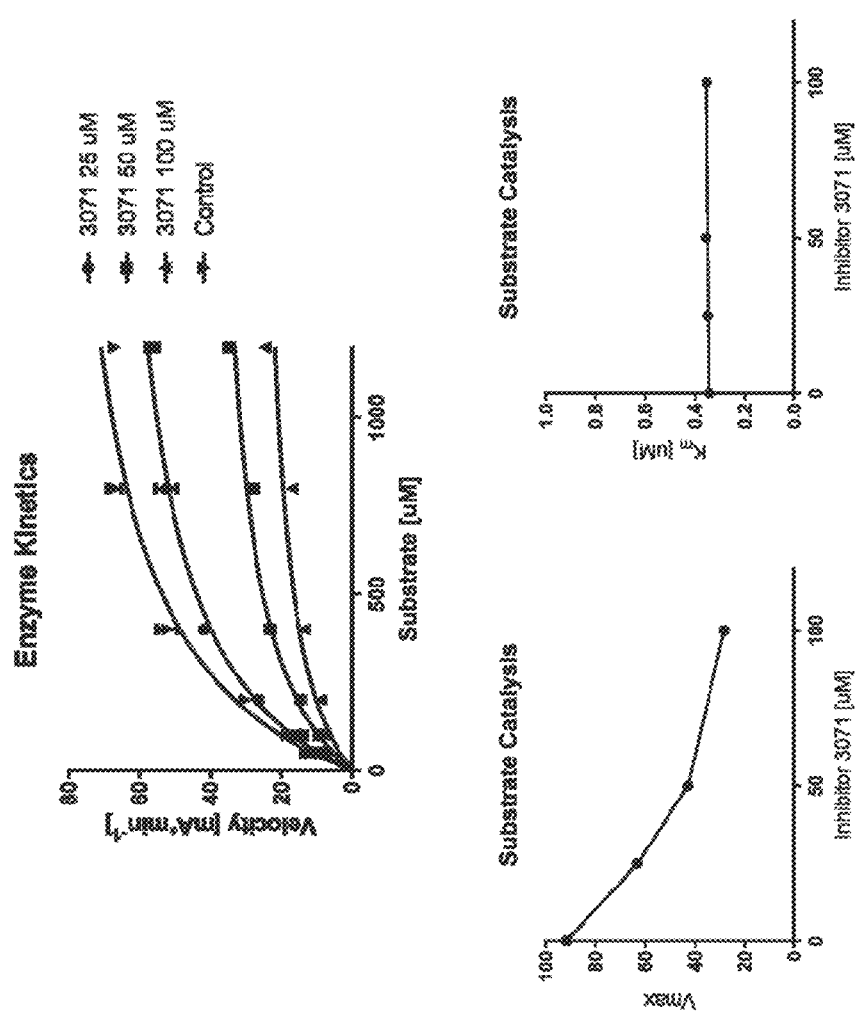
FIG. 7 shows the results of a mechanistic study on DJ001.

Substrate titration of PTPσ showed that DJ001 (compound 3071) is a classical noncompetitive inhibitor that inhibits substrate catalysis ($V_{max}$) but not substrate binding (constant $K_m$). Plots of $V_{max}$ and $K_m$ as a function of DJ001 concentration are shown in FIG. 7.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of promoting the self-renewal or regeneration of hematopoietic stem cells, comprising administering to a subject a therapeutically effective amount of a compound having the structure of formula (I) or a pharmaceutically acceptable salt thereof:

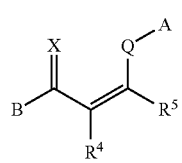

wherein:

A is selected from alkyl, alkoxy, cycloalkyl, cycloalkenyl, heterocyclyl, aryl, aralkyl, heteroaryl, and heteroaralkyl;

B is aryl or heteroaryl;

$R^4$ and $R^5$ are each independently selected from H, alkyl, alkenyl, alkynyl, alkoxy, cycloalkyl, heterocyclyl, aryl, heteroaryl, sulfonyl, and halo, or $R^4$ and $R^5$ together with the ethylene moiety that separates them may form a ring;

X is selected from O, S, or $NR^a$;

Q is selected from O, S, or $NR^a$; and each instance of $R^a$ is selected from H, alkyl, alkenyl, alkynyl, hydroxy, alkoxy, silyloxy, cycloalkyl, cycloalkenyl, heterocyclyl, aryl, heteroaryl, amino, sulfonyl, carbonyl, nitro, halo and cyano, or, when X and Q are both $NR^a$, two occurrences of $R^a$ together represent a single bond between X and Q.

2. The method of claim 1, wherein B is not 3,4-dichlorophenyl; and if A is phenyl and B is unsubstituted phenyl, then A is substituted with at least one substituent selected from alkyl, alkenyl, alkynyl, alkoxy, cycloalkyl, heterocyclyl, aryl, heteroaryl, amino, sulfonyl, carbonyl, halo and cyano.

3. The method of claim 1, wherein A is selected from alkyl, cycloalkyl, cycloalkenyl, or heterocyclyl.

4. The method of claim 2, wherein A is selected from methyl, ethyl, propyl, cyclopropyl, n-butyl, sec-butyl, tert-butyl, cyclobutyl, cyclopentyl, cyclohexyl, piperidinyl, or piperazinyl.

5. The method of claim 2, wherein A is selected from aryl, aralkyl, heteroaryl, or heteroaralkyl.

6. The method of claim 2, wherein A is selected from phenyl, benzyl, furanylmethyl, naphthyl, or benzodioxole.

7. The method of claim 1, wherein A is substituted with at least one substituent selected from alkyl, alkenyl, alkynyl, alkoxy, cycloalkyl, heterocyclyl, aryl, heteroaryl, amino, sulfonyl, carbonyl, halo and cyano.

8. The method of claim 1, wherein B is selected from phenyl, furanyl, cyclohexyl, thiophene, or naphthyl.

9. The method of claim 1, wherein $R^4$ and $R^5$ are each independently selected from H, alkyl, or cycloalkyl; or $R^4$ and $R^5$ together with the ethylene moiety that separates them form a phenylene ring.

10. The method of claim 1, wherein the compound has the structure of formula (II) or a pharmaceutically acceptable salt or prodrug thereof:

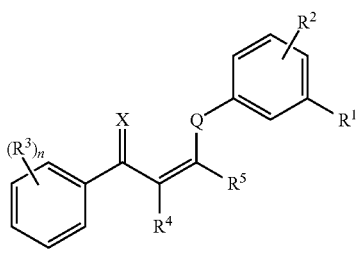
(II)

wherein:

R[1] and R[2] are independently selected from H, alkyl, alkenyl, alkynyl, hydroxy, alkoxy, silyloxy, cycloalkyl, heterocyclyl, aryl, heteroaryl, amino, sulfonyl, carbonyl, nitro, halo and cyano;

n is 0, 1, 2, 3, 4, or 5;

each instance of R[3] is independently selected from alkyl, alkenyl, alkynyl, hydroxy, alkoxy, cycloalkyl, cycloalkenyl, heterocyclyl, aryl, heteroaryl, amino, sulfonyl, carbonyl, nitro, halo and cyano; and R[4] and R[5] are each independently selected from H, alkyl, alkenyl, alkynyl, alkoxy, cycloalkyl, heterocyclyl, aryl, heteroaryl, sulfonyl, and halo, or R[4] and R[5] together with the ethylene moiety that separates them may form a ring.

11. The method of claim 10, wherein the compound has the structure of formula (IIb) or (IIc), or a pharmaceutically acceptable salt or prodrug thereof:

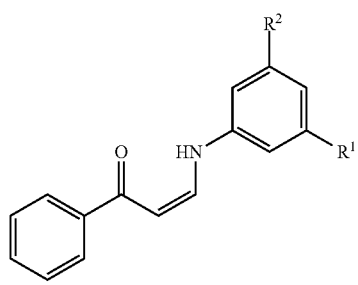
(IIb)

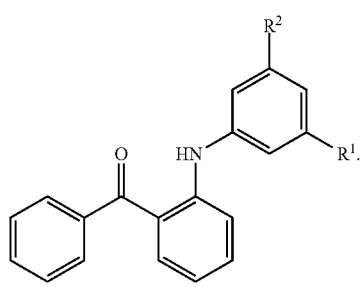
(IIc)

12. The method of claim 10, R[1] is selected from H, alkyl, alkenyl, alkynyl, hydroxy, alkoxy, cycloalkyl, heterocyclyl, aryl, heteroaryl, amino, sulfonyl, carbonyl, nitro, halo and cyano; and R[2] is selected from alkyl, alkenyl, alkynyl, alkoxy, cycloalkyl, heterocyclyl, aryl, heteroaryl, amino, sulfonyl, carbonyl, halo and cyano.

13. The method of claim 1, wherein the compound has the structure of formula (III), formula (IIIa), or a pharmaceutically acceptable salt or prodrug thereof:

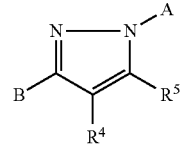
(III)

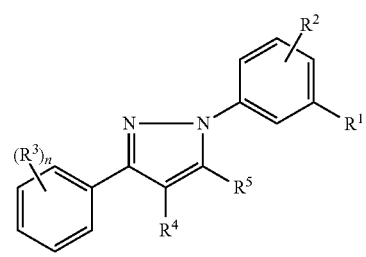
(IIIa)

wherein:

R[1] and R[2] are independently selected from H, alkyl, alkenyl, alkynyl, hydroxy, alkoxy, silyloxy, cycloalkyl, heterocyclyl, aryl, heteroaryl, amino, sulfonyl, carbonyl, nitro, halo and cyano;

n is 0, 1, 2, 3, 4, or 5;

each instance of R[3] is independently selected from alkyl, alkenyl, alkynyl, hydroxy, alkoxy, cycloalkyl, cycloalkenyl, heterocyclyl, aryl, heteroaryl, amino, sulfonyl, carbonyl, nitro, halo and cyano; and R[4] and R[5] are each independently selected from H, alkyl, alkenyl, alkynyl, alkoxy, cycloalkyl, heterocyclyl, aryl, heteroaryl, sulfonyl, and halo, or R[4] and R[5] together with the ethylene moiety that separates them may form a ring.

14. The method of claim 1, wherein the compound is

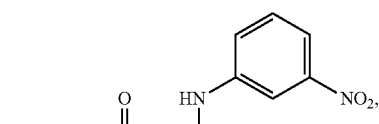

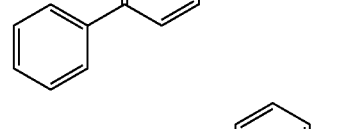

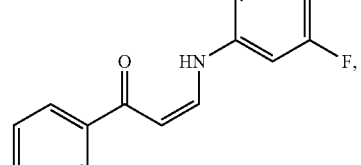

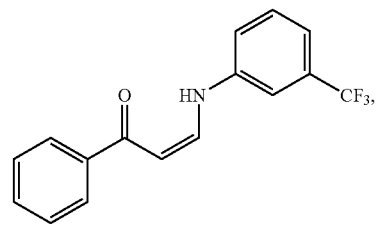

-continued
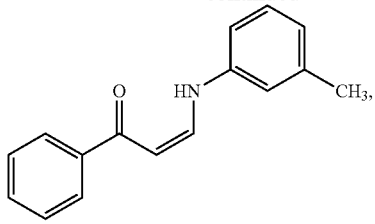
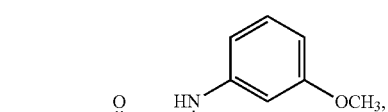
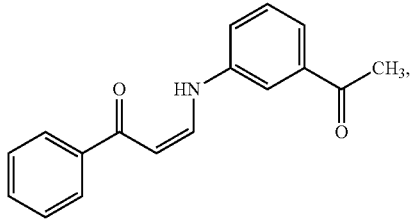
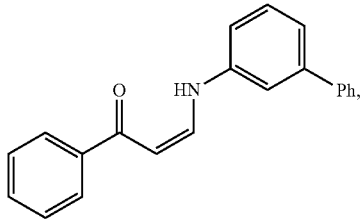
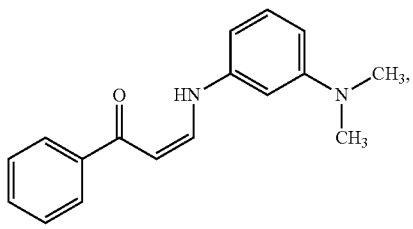
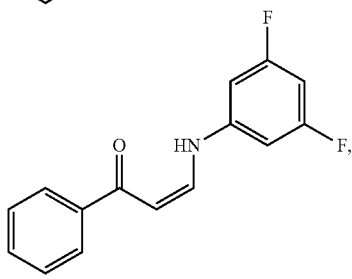
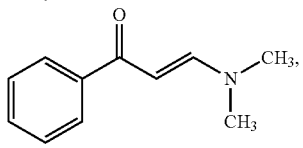
-continued
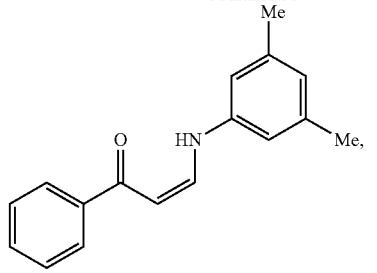
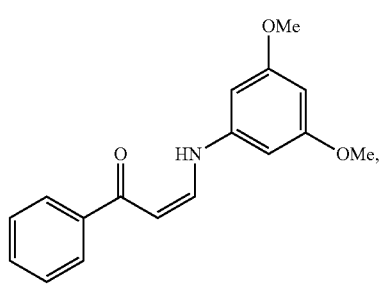
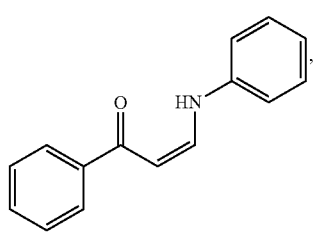
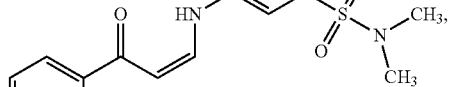
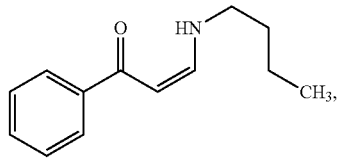

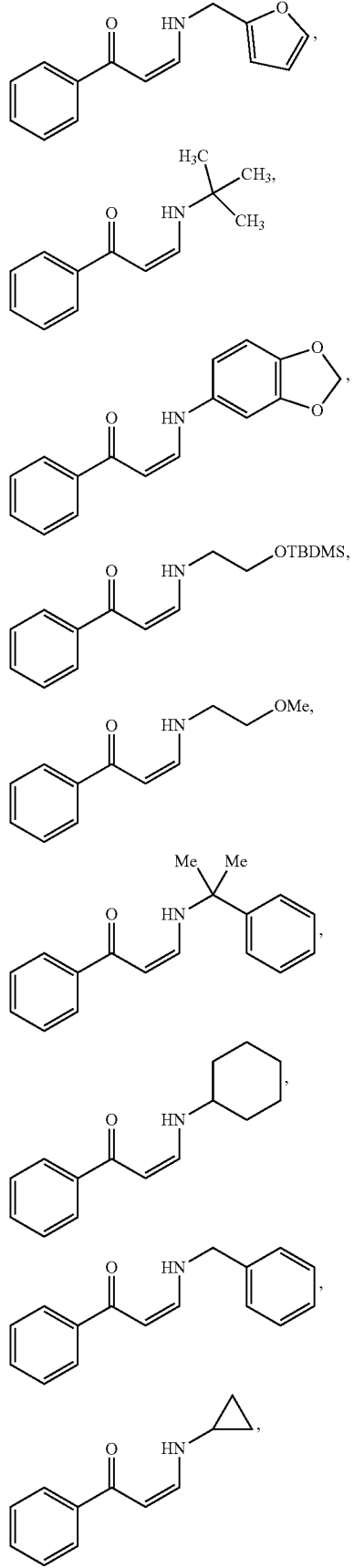
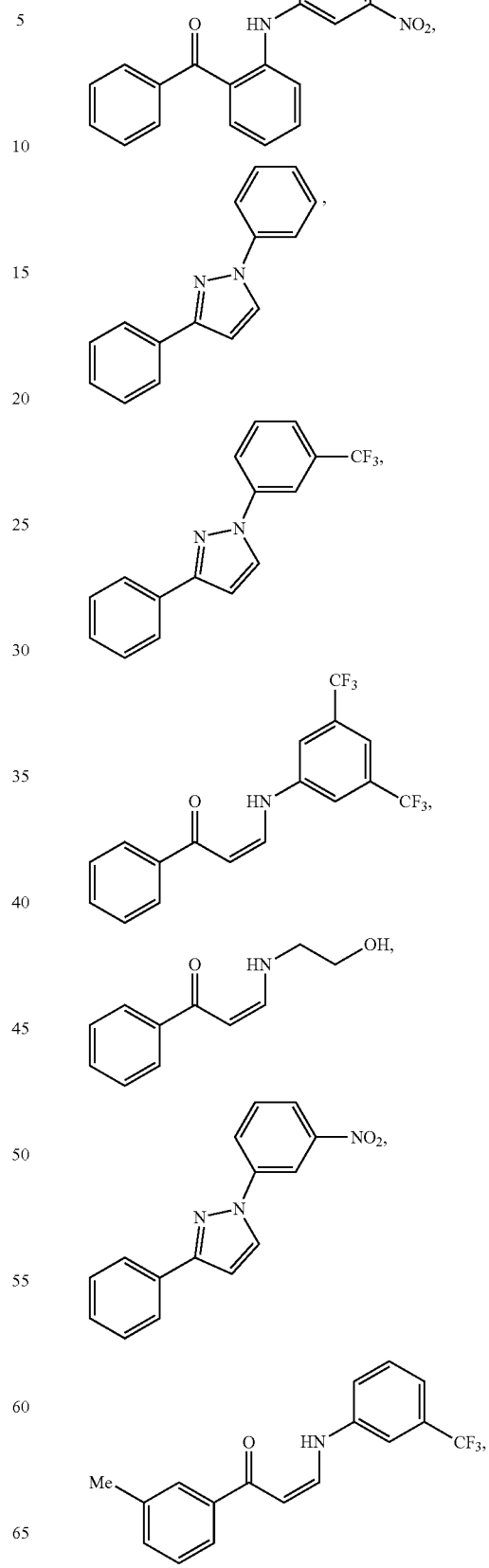

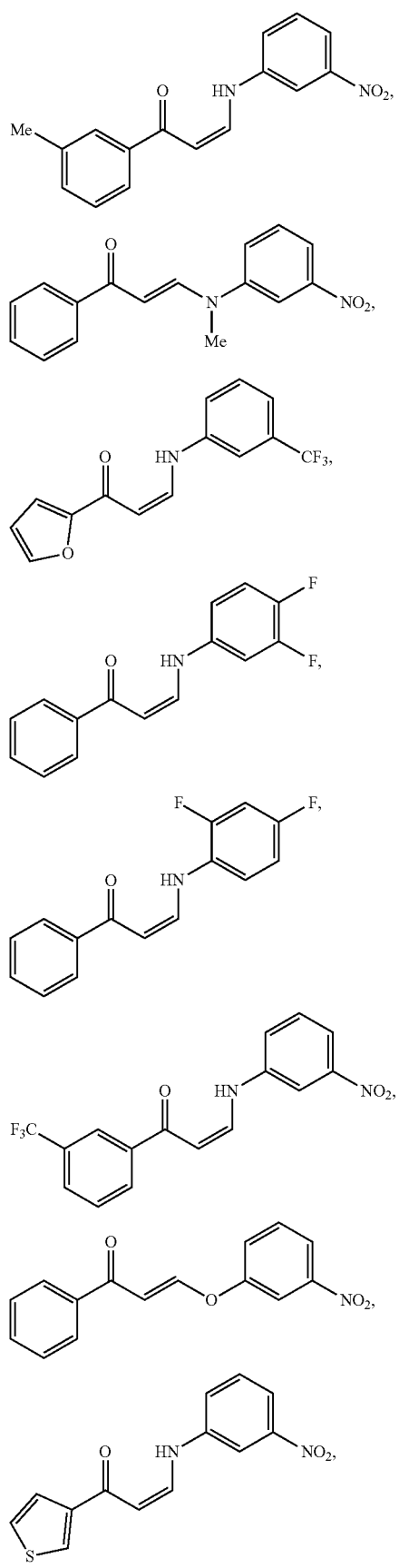
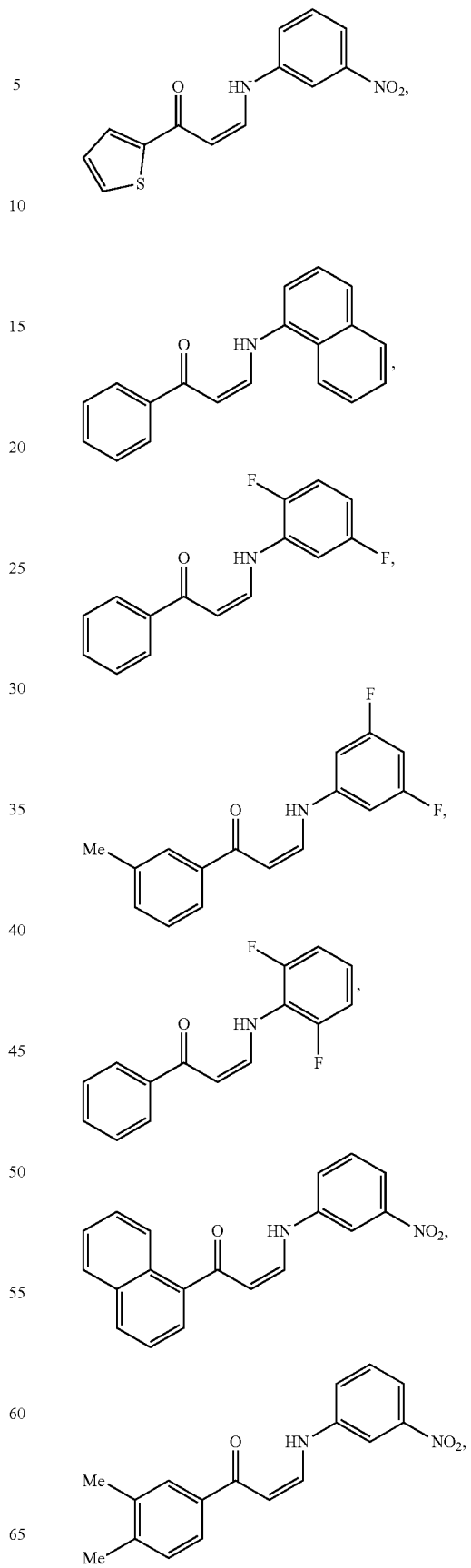

-continued

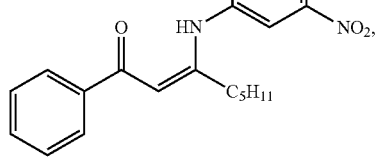

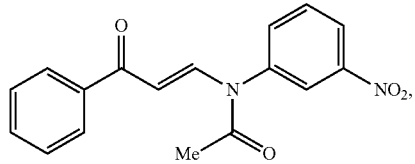

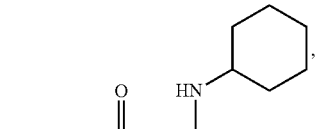

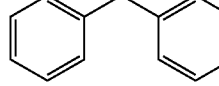

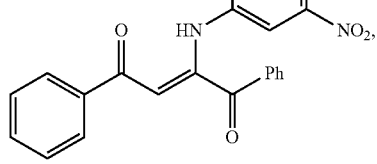

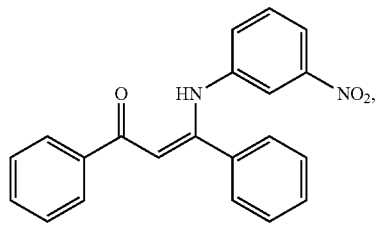

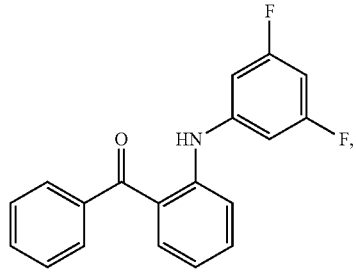

-continued

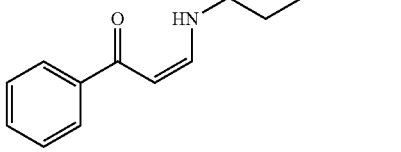

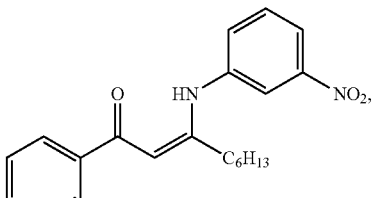

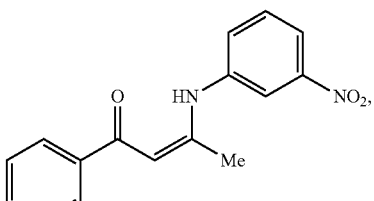

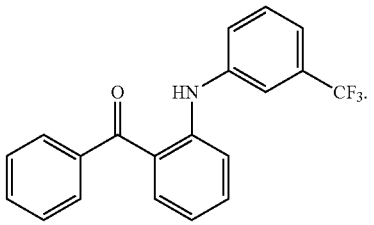

or a pharmaceutically acceptable salt.

15. The method of claim 1, wherein the subject is myelosuppressed.

16. The method of claim 1, wherein the subject has received or is receiving myelosuppressive chemotherapy or radiotherapy, has undergone or is undergoing hematopoietic cell transplantation, or is suffering from with aplastic anemia or a degenerative hematologic disease.

* * * * *

UNITED STATES PATENT AND TRADEMARK OFFICE
CERTIFICATE OF CORRECTION

Page 1 of 1

PATENT NO. : 10,822,299 B2
APPLICATION NO. : 16/304427
DATED : November 3, 2020
INVENTOR(S) : John P. Chute et al.

It is certified that error appears in the above-identified patent and that said Letters Patent is hereby corrected as shown below:

In the Claims

In Claim 13, Column 61, Line 66 cancel the text:
"formula (Ma),"
And insert:
-- formula (IIIa), --

Signed and Sealed this
Eleventh Day of May, 2021

Drew Hirshfeld
*Performing the Functions and Duties of the
Under Secretary of Commerce for Intellectual Property and
Director of the United States Patent and Trademark Office*